(12) United States Patent
Brasch et al.

(10) Patent No.: US 7,812,042 B2
(45) Date of Patent: Oct. 12, 2010

(54) PHARMACEUTICAL COMPOSITIONS AND THERAPEUTIC APPLICATIONS FOR THE USE OF A NOVEL VITAMIN $B_{12}$ DERIVATIVE, N-ACETYL-L-CYSTEINYLCOBALAMIN

(75) Inventors: Nicola E. Brasch, Kent, OH (US);
Catherine Stephanie Birch, Cheshire (GB); John Henry Howatson Williams, Corwen (GB)

(73) Assignees: Kent State University, Kent, OH (US); University of Chester, Chester (GB)

( * ) Notice: Subject to any disclaimer, the term of this patent is extended or adjusted under 35 U.S.C. 154(b) by 475 days.

(21) Appl. No.: 11/903,066

(22) Filed: Sep. 20, 2007

(65) Prior Publication Data
US 2008/0076733 A1 Mar. 27, 2008

Related U.S. Application Data

(60) Provisional application No. 60/846,435, filed on Sep. 22, 2006.

(51) Int. Cl.
*A61K 31/4184* (2006.01)
*A61K 31/28* (2006.01)
*C07D 235/08* (2006.01)
*C07F 15/06* (2006.01)

(52) U.S. Cl. ............... 514/367; 514/501; 548/108; 548/109; 548/305.1; 556/138

(58) Field of Classification Search .......... None
See application file for complete search history.

(56) References Cited

U.S. PATENT DOCUMENTS 7,709,460 B2 * 5/2010 McCaddon .......... 514/52

FOREIGN PATENT DOCUMENTS

WO  WO02/087593  * 11/2002

OTHER PUBLICATIONS

2006 Chemical Abstracts Catalog, published 2006 by Chemical Abstracts Service, p. 52.*
Merriam-Webster's Collegiate Dictionary, Tenth Edition, published 1998 by Merriam-Webster, incorporated, p. 924.*
Richard B. Silverman, The Organic Chemistry of Drug Design and Drug Action, published 1992 by Academic Press, pp. 4-47.*
Suarez-Moriera et al., "A simple, convenient method to synthesize cobalamins: synthesis of homocysteinylcobalamin, N-acetylcysteinylcobalamin, 2-N-acetylamino-2-carbomethoxyethanethiolatocobalamin, sulfitocobalamin and nitrocobalamin" Dalton Transcations (2006) pp. 5269-5277.*
Herrmann et al., "Significance of Hyperhomocysteinemia" Clin. Lab. (2006) vol. 52 pp. 367-374.*
Willcox et al., "Antioxidants and Prevention of Chronic Disease" Critical Reviews in Food Science and Nutrition (2004) vol. 44 No. 4 pp. 275-295.*
McCaddon et al., "Co-administration of N-acetylcysteine, vitamin B12 and folate in cognitively impaired hyperhomocysteinaemic patients" International Journal of Geriatric Psychiatry (2005) vol. 20, pp. 998-1000.*
Poster, Glutathionylcobalamin and N-Acetyl-L-Cysteinylcobalamin Protect Endothelial Cells from Homocysteine-Induced Oxidant Stress and Increase Intracellular Glutathione, Birch et al., University of Chester and Kent State University—Jun. 2007 Saarbrüecken, Germany.

* cited by examiner

*Primary Examiner*—Eric S Olson
(74) *Attorney, Agent, or Firm*—Hudak, Shunk & Farine Co. LPA

(57) ABSTRACT

Therapeutic applications, such as prevention, treatment and supplementation, for the use of novel and other thiolatocobalamins to protect human cells against the effects of oxidative stress. In particular, this invention relates to the use of a novel synthetic thiolatocobalamin, N-acetyl-L-cysteinylcobalamin (NACCbl) to protect animal cells against oxidative stress damage. This invention also relates to the use of thiolatocobalamins, such as NACCbl, in lieu of current, commercially available forms of vitamin $B_{12}$ for the treatment and prevention of conditions associated with oxidative stress damage and for dietary supplementation.

17 Claims, 12 Drawing Sheets

Panel A: Hsp32

Panel B: Hsp70

Panel C: β-actin

PHARMACEUTICAL COMPOSITIONS AND THERAPEUTIC APPLICATIONS FOR THE USE OF A NOVEL VITAMIN $B_{12}$ DERIVATIVE, N-ACETYL-L-CYSTEINYLCOBALAMIN

CROSS-REFERENCE

This application claims priority to U.S. Provisional Application Ser. No. 60/846,435 filed on Sep. 22, 2006.

FIELD OF THE INVENTION

This invention relates to compositions having therapeutic applications, such as prevention, treatment and supplementation, for the use in protecting animal, and in particular, human cells against the effects of oxidative stress. This invention relates to a novel synthetic thiolatocobalamin, N-acetyl-L-cysteinylcobalamin (NACCbl) which can be used to protect human cells against oxidative stress damage. This invention also relates to the use of thiolatocobalamins as a pharmaceutical composition and as a dietary supplement, such as NAC-Cbl, in lieu of current, commercially available forms of vitamin $B_{12}$, for the treatment and prevention of conditions associated with oxidative stress damage.

BACKGROUND OF THE INVENTION

Three forms of vitamin $B_{12}$ have long been recognized to occur in biology, aquacobalamin/hydroxycobalamin, methylcobalamin (MeCbl) and adenosylcobalamin (AdoCbl) (Golding, B. T. *Chem. Brit.* 1990, 950). (See Formula I). Methylcobalamin (MeCbl) and adenosylcobalamin (AdoCbl) play crucial roles in the $B_{12}$-dependent enzyme reactions and are frequently referred to as the $B_{12}$ co-enzymes. Two known $B_{12}$-dependent enzymes exist in humans: methionine synthase, which is methylcobalamin (MeCbl)-dependent, and methylmalonyl-coenzyme A mutase, which is adenosylcobalamin (AdoCbl)-dependent. (Dolphin, D. (ed). $B_{12}$; John Wiley & Sons, Inc.: New York, USA, 1982; Banerjee, R. (ed.) *Chemistry and Biochemistry of $B_{12}$*; John Wiley & Sons, Inc.: New York, USA, 1999). In short, methionine synthase and methylmalonyl-CoA mutase require the vitamin $B_{12}$ derivatives methylcobalamin (MeCbl) and adenosylcobalamin (AdoCbl), respectively, for certain enzymatic reactions in the body. For example, in the MeCbl-dependent methionine synthase reaction, a methyl group is transferred from methyl-tetrahydrofolate (a metabolite of folate) to homocysteine (Hcy) via MeCbl to give methionine and tetrahydrofolate. This reaction results in the conversion of homocysteine, an amino acid found in humans which has destructive, oxidative properties, back to methionine. This reaction has received much attention in the medical literature in recent years, because its impairment can lead to elevated levels of homocysteine, which is associated with an increased risk of cardiovascular, cerebrovascular and peripheral vascular disease, and other pathological conditions which are discussed below.

Thiol derivatives of $B_{12}$, thiolatocobalamins, were first identified in the 1960's, but have not attracted much attention until recently. They are characterized by having a cobalt-sulphur bond in the upper (beta) axial position. (See Formula I). Glutathionylcobalamin (GSCbl (or GluSCbl), a thiolatocobalamin) has been recently isolated from mammalian cells. A method for preparing glutathionylcobalamin is the subject of U.S. Pat. No. 7,030,105, the contents of which are incorporated herein by reference.

Glutathionylcobalamin (GSCbl) is an important cobalamin metabolite in mammals and is more active than other cobalamins in promoting methionine synthase activity in rabbit spleen extracts. It has been proposed that, in vivo, GSCbl (or a closely related thiolatocobalamin adduct) is a precursor of the two coenzyme forms of vitamin $B_{12}$—AdoCbl and MeCbl. An alternative role for GSCbl was also recently proposed, in which the formation of GSCbl prevents $B_{12}$ from being scavenged by xenobiotics.

The exact biochemical pathway(s) that lead to the incorporation of cobalamins into the $B_{12}$-dependent enzymes have not yet been elucidated. It is known that thiolatocobalamins can be reduced by free thiols, yielding cob(I)alamin species, which can in turn be methylated by S-adenosylmethionine to form methylcobalamin. Whether this is an important biochemical pathway in humans needs further study.

A variety of thiolatocobalamins have been synthesized. Recently, simple synthetic methods have been reported for the preparation of three additional thiolatocobalamins—D,L-homocysteinyl-cobalamin (HcyCbl), the sodium salt of N-acetyl-L-cysteinylcobalamin (Na[NACCbl]), and 2-N-acetylamino-2-carbomethoxy-L-ethanethiolatocobalamin (NACMECbl). (Suarez-Moreira, E., Hannibal, L., Smith, C., Chavez, R., Jacobsen, D. W., and Brasch, N. E., Dalton Trans., in press. However GSCbl is the only thiolatocobalamin that has been isolated in mammals to date. Furthermore, prior to this synthesis, Na[NACCbl] and NACMECbl were not even reported to exist.

Formula I, below, depicts the structures of vitamin $B_{12}$, including the two coenzyme forms of vitamin $B_{12}$ and related $B_{12}$ derivatives found in humans, all commonly referred to as the cobalamins.

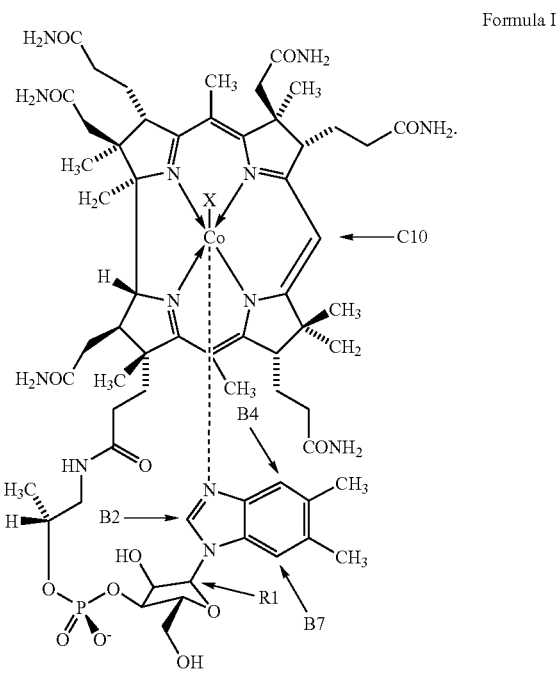

Formula I

Structures of naturally occurring cobalamins: X = 5′-deoxyadenosyl, adenosylcobalamin (coenzyme $B_{12}$); X = $CH_3$, methylcobalamin; X = $H_2O/OH^-$; aquacobalamin/hydroxycobalamin; X = $SO_3^{2-}$, sulfitocobalamin; X = $NO_2^-$, nitrocobalamin; X = $CN^-$, cyanocobalamin; X = glutathione, glutathionylcobalamin. The positions of the protons that resonate in the aromatic region in the $^1H$ NMR spectrum of cobalamins (B2, B4, B7, R1 and C10) are also shown.

The cobalamins belong to a family of compounds known as the corrinoids, which differ from one another in the specific nucleotide occupying the α axial site of the cobalt-corrin complex. The α (or lower) axial site is occupied by an intramolecularly-bound 5,6-dimethylbenzimidazole, and the β (or upper) axial site can be occupied by a variety of ligands. The various thiol ligand structures for the thiolatocobalamins mentioned herein are shown below.

Structure of the thiol ligands

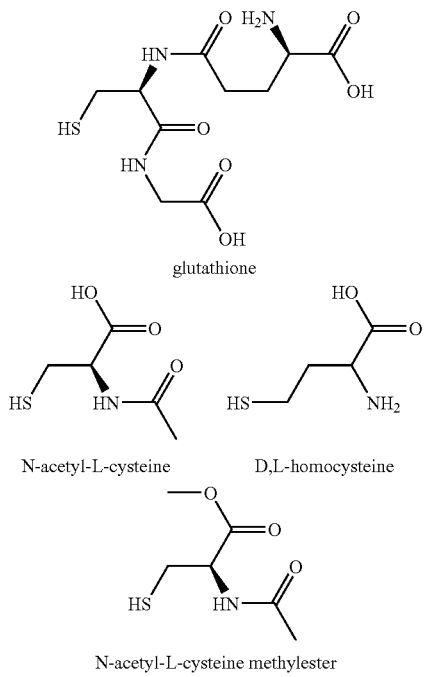

glutathione

N-acetyl-L-cysteine    D,L-homocysteine

N-acetyl-L-cysteine methylester

It is known that vitamin $B_{12}$ and its derivatives play key roles in human, animal and microbial metabolism. In humans, vitamin $B_{12}$ helps maintain healthy nerve cells and red blood cells. It is also needed to produce DNA, the genetic material in all cells. (National Institutes of Health, Office of Dietary Supplements, Dietary Fact Sheet: Vitamin $B_{12}$). Cobalamins (Cbls) are bound to protein in food, and hydrochloric acid in the stomach releases vitamin $B_{12}$ from proteins during digestion. Once released, Cbls combine with a protein known as salivary haptocorrin (HC, also known as R-binder). Upon pancreatic proteolytic degradation of HC, Cbl is transferred in the duodenum to intrinsic factor (IF), which can then be absorbed by the GI tract. Cbl is transferred to transcobalamin (TC, TCII) within enterocytes. A substantial portion of TC-Cbl entering the portal vein after absorption is cleared by hepatocytes. Any free Cbl entering the circulation binds to either TC or HC.

Vitamin $B_{12}$ deficiencies can occur in humans in a number of circumstances. Deficiencies can occur from malabsorption problems (damage to the GI tract lining, achlorhydria, inflammatory bowel conditions, infections, lack of intrinsic factor or other genetic anomalies), lack of a diet rich in vitamin $B_{12}$, or the inability to utilize absorbed vitamin $B_{12}$ and enzymatic or amino acid deficiencies. Certain drugs can also interfere with the absorption of vitamin $B_{12}$.

Vitamin $B_{12}$ deficiency can manifest in several different ways, including but not limited to anemias (including megaloblastic anemia also known as pernicious anemia), weakness, fatigue, weight loss, neurological changes, such as neuropathies (numbness and tingling), depression, confusion, and cognitive decline (such as loss of memory and dementia).

Vitamin $B_{12}$, along with folate and vitamin $B_6$, are involved in homocysteine metabolism. Homocysteine is a non-protein amino acid reversibly formed and secreted during human metabolism. Homocysteine is, however, a neurotoxin, and an abnormal increase in plasma homocysteine levels has been implicated in many pathological conditions, such as cardio-vascular disease, neural tube defects, osteoporosis, stroke and other cerebrovascular disease, peripheral vascular disease, and certain forms of glaucoma and is now recognized in Alzheimer's disease. (Tchantchou, F., "Homocysteine metabolism and various consequences of folate deficiency". *J. Alzheimer's Dis.* August 2006; Vol. 9, No. 4: 421-27). Homocysteine is eliminated from the body and is regulated by the transmethylation and transsulfuration pathways.

Homocysteine, among other reactive species, plays a key role in inducing oxidative stress. Oxidative stress can be defined as a harmful condition that occurs when there is an excess of free radicals, a decrease in antioxidants, or both. (E.g., Halliwell B. Introduction: Free Radicals and Human Disease—Trick or Treat? In: Thomas, C. E., Kalyanaraman, B. (ed.) Oxygen Radicals and the Disease Process. $1^{st}$ ed. Amsterdam. Harwood Academic Publishers. 1997. pp. 1-14). Free radicals cause damage to cells by attacking their lipids, proteins and DNA components. A free radical is any species that contains one or more unpaired electrons, which makes it more reactive so that it can react with other species to form new free radicals. (Goodall, H. Oxidative stress: an overview.) It is this cycle that can lead to damage to cells in the body from prolonged exposure to free radicals.

The term reactive species is used to describe free radicals and other molecules that are themselves easily converted to free radicals or are powerful oxidizing agents. (Id.) Hydrogen peroxide is another example of a reactive species found intracellularly and extracellularly in humans.

It is known that a deficiency of vitamin $B_{12}$, folate, or vitamin $B_6$ may increase blood levels of homocysteine. Studies have shown that the reverse is also true. It was recently reported that vitamin $B_{12}$ and folic acid supplements decreased homocysteine levels in subjects with vascular disease and in young adult women, with the most significant drop in homocysteine levels being seen when folic acid was taken alone (Bronstrup, A. et al. "Effects of folic acid and combinations of folic acid and vitamin $B_{12}$ on plasma homocysteine concentrations in healthy, young women." *Am J Clin Nutr* 1998; 68: 1104-10; Clarke, R. "Lowering blood homocysteine with folic acid based supplements. *Brit Med J* 1998; 316: 894-98). It has also been reported that a significant decrease in homocysteine levels occurred in older men and women who took a multivitamin/multimineral supplement for 8 weeks (McKay, D. et al. "Multivitamin/mineral Supplementation Improves Plasma B-Vitamin Status and Homocysteine Concentration in Healthy Older Adults Consuming a Folate-Fortified Diet." *J. Nutrition* 200; 130: 309-96).

A question has been raised as to whether homocysteine levels correlate with actual disease, disease risk or are simply a marker reflecting an underlying process such as oxidative stress which is responsible for both high homocysteine levels and the development of disease. (Seshadri, S. "Elevated Plasma Homocysteine Levels: Risk Factor or Risk Marker for the Development of Dementia and Alzheimer's Disease". *J. Alzheimer's Dis. August* 2006; Vol. 9, No. 4: 393-398.) Furthermore, McCaddon et al. note that these mechanisms are not necessarily mutually exclusive—for example, elevated homocysteine levels may perhaps be both a cause and consequence of oxidative stress (McCaddon et al. "Functional Vitamin $B_{12}$ deficiency and Alzheimer's Disease. *Neurology* 2002; 58 (9): 1395-99).

It is well-accepted that many vitamin $B_{12}$-related conditions, regardless of cause, can be easily (and reversibly) treated by administering vitamin $B_{12}$ or its hydroxycobalamin derivative, either orally or by injection into muscle tissue. As suggested by the above studies, vitamin $B_{12}$ may also play a role in conditions associated with oxidative stress by decreasing levels of homocysteine or other reactive species.

Thiolatocobalamins present useful therapeutic alternatives to vitamin $B_{12}$ or hydroxycobalamin administration or supplementation. McCaddon and coworkers suggested that GSCbl and related thiolatocobalamins might be more effective than currently available pharmaceutical $B_{12}$ forms (CNCbl and hydroxycobalamin) in treating of conditions associated with oxidative stress such as Alzheimer's disease (AD) and other neurological diseases (McCaddon, A., Regland, B., Hudson, P.; Davies, G. *Neurol* 2002; 58: 1395-1399). Numerous studies show that oxidative stress is an important neurodegenerative element in AD and several other neurological diseases. Glutathionylcobalamin is a naturally occurring intracellular form of cobalamin and is more readily absorbed and retained longer than cyanocobalamin. It has been proposed that, in vivo, GSCbl is an intermediate in the conversion of biologically inactive cyanocobalamin to the active coenzyme forms adenosylcobalamin and methylcobalamin. The reducing agent glutathione (GSH) is required for the formation of GSCbl, and is likely to be present in lower levels in AD patients as compared with healthy individuals due to oxidative stress. Thus, GSCbl has the potential to offer a valuable, direct source of cobalamin in therapeutic applications requiring administration of a vitamin $B_{12}$ derivative. Furthermore, reduced glutathione levels are associated with a wide range of pathophysiological conditions, including liver failure, malignancies, HIV infection, pulmonary disease, and Parkinson's disease. The following list is for example purposes only and, although extensive, is not exhaustive: Acetaminophen poisoning, Attention Deficit Disorder, Autistic Spectrum Disorders, Addison's disease, aging, Acquired Immunodeficiency Syndrome, Amyotrophic lateral sclerosis, ankylosing spondylitis, arteriosclerosis, arthritis (rheumatoid), asthma, autoimmune disease, Behcet's disease, burns, cachexia, cancer, candida, cardiomyopathy, chronic fatigue syndrome, chronic obstructive pulmonary disease, chronic renal failure, colitis, coronary artery disease, cystic fibrosis, diabetes mellitus, Crohn's disease, Down's syndrome, eczema, emphysema, Epstein Barr viral syndrome, fibromyalgia, glaucoma, Goodpasture syndrome, Grave's disease, hypercholesterolaemia, herpes, viral/bacterial/fungal infections, inflammatory bowel disease, systemic lupus erythematosis, senile and diabetic macular degeneration, malnutrition, Meniere's disease, Multiple Sclerosis, Myasthenia Gravis, neurodegenerative diseases, nutritional disorders, pre-eclampsia, progeria, psoriasis, rheumatic fever, sarcoidosis, scleroderma, shingles, stroke, vasculitis and vitiligo.

McCaddon and Davies recently reported on observations concerning the co-administration of N-acetyl-L-cysteine (NAC, a glutathione precursor and potent antioxidant) with B vitamin supplements in cognitively impaired patients, all of whom had high serum homocysteine levels and two of whom had low reported glutathione levels. Improvements in agitation, alertness, and cognitive function were observed in these patients. (McCaddon, A. and Davies, G. "Co-administration of N-acetylcysteine, vitamin $B_{12}$, and folate in cognitively impaired hyperhomocysteinaemic patients." *Int. J. Geriatr Psychiatry* 2005; 20: 998-1000).

McCaddon also reported more recent observations concerning additional hyperhomocysteinanemic patients with cognitive impairment. The case reports demonstrate an apparent clinical efficacy of the addition of 600 mg N-acetyl-L-cysteine (NAC) to $B_{12}$ and/or folate regimens. (McCaddon, A. "Homocysteine and cognitive impairment; a case series in a General Practice setting." *Nutrition Journal* 2006; 5:6).

In view of the potential benefits reported with the use of glutathionylcobalamin, other thiolatocobalamins are also of interest. In particular, the novel compound Na[NACCbl] and other salts of NACCbl are of interest as a potential treatment or supplement, especially considering the above-noted observations associated with co-administrating hydroxycobalamin and N-acetyl-L-cysteine to Alzheimer's patients. There is an impetus to further test these novel, synthetic compounds for biological activity.

An understanding of the stability of thiolatocobalamins is essential if these compounds are to be used for treatment or supplemental applications. It is also important when exploring the biological relevance of these compounds. A range of thiolatocobalamins have been synthesized, some novel, and studies have been initiated on the stability and reactivity of these compounds as well. Interestingly, the stability of a specific thiolatocobalamin is very dependent on the thiol itself, and can vary over several orders of magnitude.

In efforts to reduce the damaging effects of oxidative stress and to establish the role of thiolatocobalamin treatment or supplementation in conditions associated with oxidative stress, there is a need to identify useful, stable and reactive thiolatocobalamin species. There is also a need not only for simple convenient methods of preparing thiolatocobalamins for use in human and animal studies, but also to develop test protocols that better define the role of oxidative stress (including the effects of reactive species such as homocysteine and hydrogen peroxide) in cell damage. Finally, there is a need to demonstrate the effects of naturally occurring and novel thiolatocobalamins on both healthy cells and those subjected to oxidative stress, including among other things increased homocysteine or $H_2O_2$ levels, in order to identify useful therapeutic applications for thiolatocobalamins.

SUMMARY OF THE INVENTION

It has been discovered that NACCbl protects cells from damage and death when exposed to oxidative stress conditions. Indeed, NACCbl may provide superior results in patients having, or prone to, oxidative stress conditions associated with neurological disease. It may also be useful for a wide range of other diseases associated with oxidative stress. NACCbl may also be a useful form of vitamin $B_{12}$ for dietary supplementation. NACCbl has been synthesized as a sodium salt (Na[NACCbl]); however, other salts of NACCbl, such for example a potassium salt, may also prove useful in the treatment of oxidative stress-related disorders or as dietary supplements and are well within the intent and spirit of the invention.

The focus of a number of studies has been on the effects of vitamin $B_{12}$ and its derivatives on homocysteine levels. It is well-recognized that the hallmark of cardiovascular disease, cerebrovascular disease and peripheral vascular disease, among others, is endothelial cell damage. By using cell model data, we have discovered that N-acetyl-L-cysteinylcobalamin, regardless of whether administered alone or in combination with folate, effectively protects endothelial cells against homocysteine-induced oxidative damage. Furthermore, N-acetyl-L-cysteinylcobalamin protects cells against hydrogen peroxide-induced oxidative damage. Importantly, this novel vitamin $B_{12}$ derivative shows superior protection compared with the currently available pharmaceutical forms of vitamin $B_{12}$ and folate and naturally occurring cobalamins.

Thus, in accordance with the invention a pharmaceutical composition or dietary supplement respectively comprising N-acetyl-L-cysteinylcobalamin is provided for the treatment of conditions of oxidative stress in animals, including mammals and birds, and specifically including humans; livestock, such as beef and diary cattle, horses, pigs, goats, rabbits and poultry; and domestic animals, such as cats and dogs. The pharmaceutical composition or dietary supplement may also comprise a folate composition and a vitamin $B_6$ composition. The pharmaceutical composition may include additional ingredients as is appropriate for the form of administration, including a pharamaceutically acceptable carrier or solvent.

Further the N-acetyl-L-cysteinylcobalamin of the pharmaceutical composition or dietary supplement may advantageously comprise a crystalline salt of N-acetyl-L-cysteinylcobalamin, and in particular may comprise a biologically acceptable salt, such as a sodium or potassium salt of said N-acetyl-L-cysteinylcobalamin.

The invention further relates to a method to treat a disease or condition associated with oxidative stress comprising administering an effective amount of N-acetyl-L-cysteinylcobalamin (including a derivative or salt thereof). This agent may be administered in combination with effective amounts of compounds known to reduce serum homocysteine levels, such as one or more of a folate compound and vitamin $B_6$. The disease or condition associated with oxidative stress may be one or more of cardiovascular disease, cerebrovascular disease, peripheral vascular disease, glaucoma, Alzheimer's disease, dementia, and combinations thereof. The invention also relates to a method for the inhibition or reduction of free radical formation comprising administering N-acetyl-L-cysteinylcobalamin (or a derivative or salt thereof), and in particular where the free radical formation is due to high hydrogen peroxide levels, or notably where the free radical is hydrogen peroxide.

DESCRIPTION OF THE INVENTION

Figure 2:
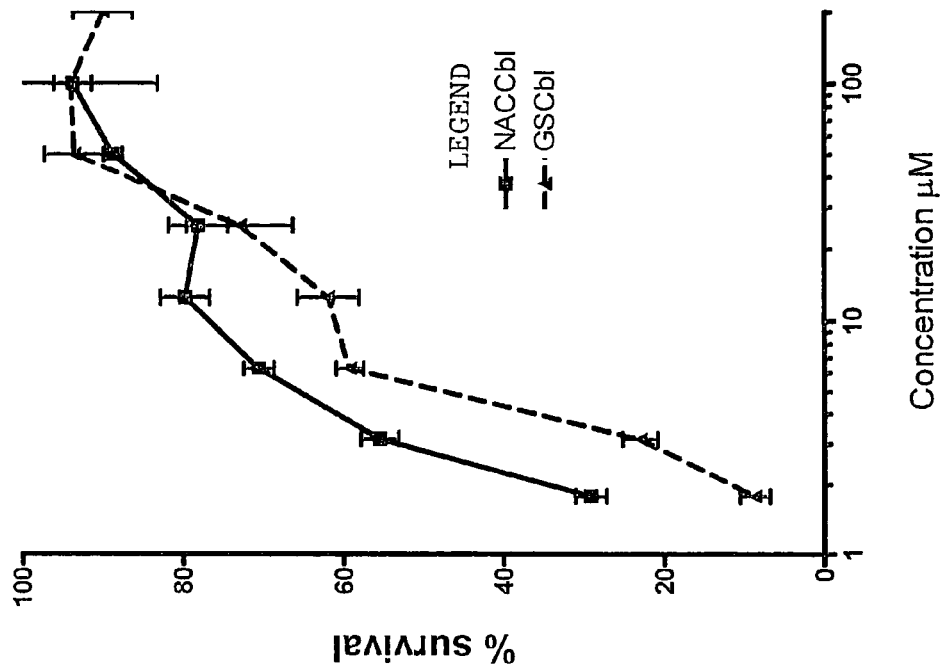
FIG. 2 is a graphic representation showing that NACCbl and GSCbl protect endothelial cells from the effect of homocysteine.

This invention relates to a novel synthetic thiolatocobalamin, N-acetyl-L-cysteinylcobalamin (NACCbl), which can be used to protect cells against oxidative stress damage. NACCbl can be a pharmaceutical composition or a dietary supplement which advantageously further comprises a folate compound which is used here to include folate and any natural isomer of reduced folate, such as (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives, as described in U.S. Pat. No. 5,997,915. A "pharmaceutical composition" is used herein to mean a composition in a biologically acceptable carrier as is appropriate for the means of administration and at a concentration to provide an acceptable dosage for the intended therapeutic or prophalatic result. A "dietary supplement" is used herein to mean a form that can be acceptably administered as a supplement to the customary dietary intake of the subject animal such as, for example, multivitamin preparations (with or without minerals and other nutrients); breakfast foods such as prepared cereals, toaster pastries and breakfast bars; infant formulas; dietary supplements and complete diet and weight-loss formulas and bars; animal feed (for example pet foods) and animal feed supplements (such as for poultry feed). The amount of the natural isomer of a reduced folate in a composition for human consumption can range between about 5% and about 200% of the daily requirement for folic acid per serving or dose. The animals to which the compositions can be applied for therapeutic effect are birds or mammals, such as livestock, domestic animal or most advantageously humans.

The invention further relates to a method of treatment of diseases of conditions related to oxidative stress comprising administering an effective amount of a composition comprising NACCbl (meaning specifically NACCbl, its derivatives and salts thereof), preferably with one or more of a folate compound (as previously discussed) and vitamin $B_6$. The term "effective amount" as used herein refers to an amount of an NACCbl sufficient to affect the symptoms due to oxidative stress or free radical presence to a statistically significant degree. The term "effective amount" therefore includes, for example, an amount sufficient to prevent or treat a condition of oxidative stress, such as dementia or stroke. The dosage ranges for the administration of NACCbl are those that produce the desired effect. Generally, the dosage will vary with the age, weight, condition, and sex of the patient. A person of ordinary skill in the art, given the teachings of the present specification, may readily determine suitable dosage ranges. The dosage can be adjusted by the individual physician in the event of any contraindications. In any event, the effectiveness of treatment can be determined by monitoring the extent of oxidative conditions or diseases by methods well known to those in the field. Moreover, the NACCbl can be applied in pharmaceutically acceptable carriers known in the art. The NACCbl can be used to treat conditions or diseases associated with oxidative stress in animals and in humans in vivo. The application can be oral, by injection, or topical, providing that in an oral administration the NACCbl is preferably protected from digestion.

The NACCbl may be administered to a patient by any suitable means, including oral, parenteral, subcutaneous, intrapulmonary, topically, and intranasal administration. Parenteral infusions include intramuscular, intravenous, intraarterial, intraperitoneal or intravitreal administration. The NACCbl may also be administered transdermally, for example in the form of a slow-release subcutaneous implant, or orally in the form of capsules, powders, or granules. Although direct oral administration may cause some loss of activity, the NACCbl could be packaged in such a way to protect the active ingredient(s) from digestion by use of enteric coatings, capsules or other methods known in the art.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, and glycerol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The NACCbl may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed from inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of the NACCbl may be controlled by altering the concentration of the macromolecule.

Another method for controlling the duration of action comprises incorporating the NACCbl or a salt or derivative thereof into particles of a polymeric substance such as a polyester, peptide, hydrogel, polylactide/glycolide copolymer, or ethylenevinylacetate copolymers. Alternatively, the NACCbl may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The present invention provides a method of preventing, treating, or ameliorating a disease that results from development of oxidative stress in the body, such as cardiovascular disease, neural tube defects, osteoporosis, stroke and other cerebrovascular disease, peripheral vascular disease, glaucoma, Alzheimer's disease and dementia, comprising administering to a subject at risk for a disease or displaying symptoms for such disease, an effective amount of NACCbl. The present invention also provides a method of preventing, treating, or ameliorating a disease that results from an increase in free radical activity, such as inflammation, oxidative stress, rheumatoid arthritis, aging, arthrosclerosis, multiple sclerosis, asthma, inflammatory bowel disease, chronic inflammatory demyelinating polyradioculoneuritis, and cancer. The term "ameliorate" refers to a decrease or lessening of the symptoms or signs of the disorder being treated. The symptoms or signs that may be ameliorated, for example, include those associated with dementia or AD.

For purposes of the inventions described herein, the structure and purity of the novel compound NACCbl (sodium salt) was characterized using UV/Vis Spectrophotometry, $^1$H NMR spectroscopy, X-ray crystallography, XAS (spectrum not shown) and ES-MS (data not shown) for purposes of providing a thorough characterization of the new compound and evaluating its purity, stability and reactivity. The synthesis and characterization of glutathionylcobalamin has been previously reported in U.S. Pat. No. 7,030,105, the entire contents of which are incorporated herein by reference The thiolatocobalamin derivative, Na[NACCbl], is synthesized herein and isolated in high purity (>95%) and in good yield (>70%). The synthesis is carried out in aqueous solution by the addition of a small excess of thiol to a highly concentrated solution of aquacobalamin, followed by the addition of acetone to precipitate the product after completion of the reaction The synthesis of the sodium salt of N-acetyl-L-cysteinyl-cobalamin (Na[NACCbl]) involves reacting a salt of hydroxycobalamin with a slight excess (i.e. from about 1.2 to about 2 or about 1.5, and preferably from about 1.2 to about 1.5 of equivalents) of N-acetyl-L-cysteine in an aqueous solvent; precipitating the formed Na[NACCbl] from the aqueous solvent, preferably by the addition of a precipitate inducing solvent; and collecting the precipitated Na[NACCbl] and all of the above steps are carried out under aerobic conditions.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers. As used herein, a salt of hydroxycobalamin refers to a compound H₂Ocbl.X (or HOCbl.HX) wherein X is a counter anion such as a halide (particularly Cl⁻) or an O-acyl group such as acetate.

The reaction is performed in an aqueous solvent, being water alone or a mixture of water and a water miscible solvent (such as MeOH, EtOH, PrOH & BuOH). Preferably the aqueous solvent is water alone. Where the reaction is carried out in a mixture of water and water miscible solvent, the proportion of water to water miscible solvent may depend on the kinetics and/or thermodynamics of the reaction. The reaction mixture may also optionally contain additional agents such as buffers, for example, MES. The resultant cobalamin derivatives may be slightly light-sensitive, therefore, preferably, the reaction is carried out under red light only conditions.

The reaction may be performed at a temperature from 0° to about 60°. The reaction may be carried out at ambient room temperature, such as from about 15° C. to about 30° C., for example about 20-25° C. The reaction is allowed to proceed for a time sufficient to achieve substantial completion. Reference to substantial completion of the reaction is intended to refer to the substantial consumption (e.g. greater than 95%) of the HOCbl.HX. Precipitation of the resultant products may be performed under cooling, for example ice cooling, eg to about −10° C. However, yield of the cobalamin products can be increased by the addition of a precipitate inducing solvent. The precipitate inducing solvent used to precipitate the formed Na[NACCbl], which is preferably a water miscible solvent less polar then water and includes alcohols (such as MeOH, EtOH, PrOH & BuOH) and acetone, is added in an amount sufficient to induce precipitation of the formed Na[NACCbl]. A preferred precipitate inducing solvent is acetone.

According to this method of synthesis, a final product with greater than 90% purity, preferably greater than about 95% purity, more preferably 97, 98 or 99% purity as determined by the any of methods described herein such as, for example, ¹H NMR spectroscopy or the dicyanocobalamin test described by Barker et al., *J. Biol. Chem.* 1960, 135, 181-190 incorporated herein by reference as if fully set forth herein. The precipitated Na[NACCbl] is collected by filtration, preferably under suction, and optionally washing the precipitate with a suitable solvent or mixture of solvents such as acetone and/or ether. In another embodiment of the invention, the precipitate can be collected by decanting off the solvents or removing them by suction. Preferably, the precipitate is further dried to remove any remaining solvent. This may be carried out by under vacuum, optionally with heating (at a temperature which does not decompose the Na[NACCbl], for example from about 25-40° C.).

Synthesis of N-acetyl-L-cysteinylcobalamin (Na[NACCbl])

The synthesis was carried out under aerobic conditions, notwithstanding the potential light sensitivity of thiolatocobalamins. A solution of N-acetyl-L-cysteine (263 μml, 284 mM, 74.7 mmol, 1.1 mol equiv.) in MES buffer (0.1 M, pH ~6) was added drop wise to a solution of HOCbl.HCl (107 mg, 67.9 mmol) in MES buffer (0.80 ml, 0.1 M, pH ~6) with stirring, and the reaction was allowed to react for 30 min at 0° C. The product precipitated upon dripping into a chilled acetone solution (−20° C.), and was filtered, washed with chilled acetone (20 ml, −20° C.) and diethyl ether (10 ml, −20° C.). The product was dried at 50° C. under vacuum (2×10⁻² mbar) overnight. Yield: 90 mg (87%). The percentage of non-corrinoid products (salts) in the product can be determined by converting the thiolatocobalamin to dicyanocobalamin after drying the product at 50° C. under vacuum ($\lambda_{367\,nm}$=30.4 mM⁻¹ cm⁻¹), and was found to be ≦5%.

Structure

UV/Vis spectrophotometry can be used to characterize thiolatocobalamins. All spectra were recorded using a Varian Cary 5000 spectrophotometer. Data in Table 1 below showed that all thiolatocobalamins have a similar electronic spectrum with characteristic bands at 333, 372, 428 and 534 nm that are in agreement with previous reports for other thiolatocobalamins.

| Cbl | γ max (nm) | | | |
|---|---|---|---|---|
| GSCbl | 333 | 372 | 428 | 534 |
| NACCbl | 333 | 372 | 428 | 534 |
| HcyCbl | 333 | 372 | 428 | 534 |
| NACMECbl [definition?] | 333 | 372 | 428 | 534 |

The ¹H NMR spectrum of the cobalamins was also recorded (500 MHz Varian spectrometer, D₂O, 25° C.). NACMECbl is 2-N-acetylamino-2-carbomethoxy-L-ethanethiolatocobalamin. Thiolatocobalamins have five characteristic signals in the aromatic region ($B_7$, $B_2$, $B_4$, $R_1$ and $C_{10}$ protons, see FIG. 1 for assignment). Table 2 below summarizes the results. It can be seen that all thiolatocobalamins have similar chemical shifts, and they are in agreement with reported values.

TABLE 2

¹H NMR Data

| | Chemical Shift (ppm) | | | | |
|---|---|---|---|---|---|
| Cobalamin | $B_7$ | $B_2$ | $B_4$ | $R_1$ | $C_{10}$ |
| GSCbl | 7.19 | 6.95 | 6.39 | 6.28 | 6.09 |
| NACCbl | 7.19 | 6.95 | 6.40 | 6.28 | 6.09 |
| HcyCbl | 7.20 | 6.95 | 6.38 | 6.28 | 6.10 |
| NACMECbl | 7.19 | 6.95 | 6.40 | 6.28 | 6.09 |

Purity

The purity of the products was also assessed by ¹H NMR spectroscopy and by the dicyanocobalamin test. All B₁₂ derivatives are converted to dicyanocobalamin ((CN)₂Cbl) upon the addition of cyanide; hence, the percentage of non B₁₂ impurities can be determined. Table 3 below shows the results obtained.

TABLE 3

Purity Assay

| Cobalamin | (CN)₂Cbl Test | ¹H NMR Spectroscopy |
|---|---|---|
| GSCbl | 99% | 98% |
| NACCbl | 95% | 98% |
| HcyCbl | 97% | 98% |
| NACMECbl | 96% | 98% |

X-Ray Diffraction Studies

Crystals of Na[NACCbl] 18H₂O were grown in water. Diffraction experiments were carried out on beamline BL11-1 at the Stanford Synchrotron Radiation Laboratory (SSRL). Data were collected on an ADSC Q-315 CCD detector using X-rays produced by a 26 pole wiggler insertion device, with a wavelength of 0.81798 Å (15160 eV) from a side scattering bent asymmetric cut Si (111) crystal monochromator. Table 4, below, shows bond length data for NACCbl. Bond length data for γ glutamylcysteinylcobalamin (γ-GluCysCbl) is also given for comparison purposes.

TABLE 4

|          | NACCbl | γ-GluCysCbl | Δ(NACCbl-γGluCysCbl) |
|----------|--------|-------------|----------------------|
| Co—S     | 2.25   | 2.27        | −0.02                |
| Co—$NB_3$ | 2.06   | 2.05        | +0.01                |
| Co—$N_{21}$ | 1.88 | 1.89        | −0.01                |
| Co—$N_{22}$ | 1.92 | 1.90        | +0.02                |
| Co—$N_{23}$ | 1.93 | 1.91        | +0.02                |
| Co—$N_{24}$ | 1.88 | 1.89        | −0.01                |

Stability Studies

The decomposition of GSCbl, NACCbl, and HcyCbl in PBS at 37° C. was monitored by UV/Vis spectrophotometry. Table 5 below shows $t_{1/2}$ and observed rate constant, $k_{obs}$, calculated for each derivative.

TABLE 5

|        | $t_{1/2}$ (hr) | $K_{obs}$ (min$^{-1}$) |
|--------|----------------|------------------------|
| GSCbl  | No decomposition within 20 hours | |
| NACCbl | No decomposition within 20 hours | |
| HcyCbl | 6.6            | 0.0018                 |

After characterization, NACCbl was subjected to several experiments to determine if it offered protection to endothelial and other cells subject to oxidative stress under variable concentrations of homocysteine or $H_2O_2$. Experiments were also conducted to determine what, if any, detrimental effects NACCbl and GSCbl have on endothelial cells at increasing concentrations. While not wishing to be bound by any specific theory, experiments were conducted to determine potential mechanisms by which NACCbl's protective effects occur. Finally, experiments were conducted to determine if NACCbl offered any advantage in protection over other thiolatocobalamins, cobalamins or folate. These experiments are set forth in the examples below.

EXAMPLES

Reagents

The conduct of the experiments required a number of reagents, which are set forth below. However, the experiments are not limited to the specific reagents listed, and other reagents, useful in the described methods, are well within the spirit and intention of the invention.

Reagents/Materials Used in Experiments

The reagents, assays, kits and other materials used in the experiments are set forth in the lists below. All chemicals were obtained from Sigma-Aldrich Company Limited, Poole, Dorset, UK, unless otherwise indicated.

Reagents:
    MegaCell® M.E.M. Media. Sigma. Product Code: M4067
    DMEM without L-glutamine and phenol red. BioWhittaker, Cambrex Bioscience, Nottingham, UK.
    FetalClone 1 Serum; Triple 0.1 μM filtered. HyClone, Logan, Utah, USA. Cat No. SH30080.03
    5-Methyltetrahydrofolic acid disodium salt: [5-Methyl-5,6,7,8-tetrahydropteroyl-L-glutamic acid disodium salt]; $C_{20}H_{23}N_7Na_2O_6$; F.W. 503.42; EC No. 2.1.1.13
    DL-Homocysteine: [2-Amino-4-mercaptobutyric acid] $HSCH_2CH_2CH(NH_2)COOH$; F.W. 135.18; EC No. 207-222-9
    Dimethyl sulfoxide: [DMSO, Methyl sulfoxide]; $(CH_3)_2SO$; F.W. 78.13; EC No. 200-664-3
    Pyridoxine: [Pyridoxol; Vitamin $B_6$]; $C_8H_{11}NO_3$; F.W. 169.18; EC No. 200-603-0
    Vitamin $B_{12}$: [CN-Cbl; Cyanocobalamin]; $C_{63}H_{88}CoN_{14}O_{14}P$; F.W. 1355.37; EC No. 200-680-0
    Methylcobalamin: $C_{63}H_{91}CoN_{13}O_{14}P$; F.W. 1344.38; EC No. 236-535-3
    Vitamin $B_{12}$ a: [Aquocobalamin chloride]; $C_{62}H_{90}ClC_oN_{13}O_{15}P$; F.W. 1382.82; EC No. 261-200-3
    Hydroxocobalamin: [Hydroxocobalamin acetate salt, Vitamin $B_{12}$a]; $C_{64}H_{91}CoN_{13}O_{16}P$; F.W. 1388.39; EC No. 236-533-2\
    Bilirubin Mixed Isomers [Bilirubin IX-alpha] $C_{33}H_{36}N_4O_6$; M.W. 584.68; EC No. 211-239-7
    Glutathionylcobalamin: GSCbl M.W. 1635.0 synthesized by the inventors as described in U.S. Pat. No. 7,030,105
    N-acetyl-L-cysteinylcobalamin: NACCbl M.W. 1491.0 synthesized by the inventors as described herein
    Quercetin dehydrate: [2-(3,4-Dihydroxyphenyl)-3,5,7-trihydroxy-4H-1-benzopyran-4-one dihydrate]; $C_{15}H_{10}O_7.2H_2O$; F.W. 338.27; EC No. 204-187-1
    Sn Protoporphyrin(IX) dihydrochloride
    8,13-Bis(vinyl)-3,7,12,17-tetramethyl-21H,23H-porphine-2,18diproprionic acid tin(IV) dichloride; [Sn(IX) PP]; $C_{34}H_{32}N_4O_4SnCl_2$; M.W. 750.26; Frontier Scientific Inc., Carnforth, UK.
    Hydrogen peroxide solution: 30% (w/w): $H_2O_2$; F.W. 34.01; EC No. 231-765-0
    Propidium iodide: [3,8-Diamino-5[3-(diethylmethylammonio)propyl]-6-phenyl-phenanthridinium diiodide]; $C_{27}H_{34}I_2N_4$; M.W. 668.41; EC No. 247-081-0
    Necrosis Inhibitor: IM 54; [2-(1H-Indol-3-yl)-3-pentylamino-maleimide]; $C_{19}H_{23}N_3O_2$; M.W. 325.4; Cat No. 480060
    Etoposide: [VP-16]; $C_{29}H_{32}O_{13}$; M.W. 588.6; EC No. 251-509-1; Calbiochem, Nottingham, UK.
    Hemin: $C_{34}H_{32}C_1FeN_4O_4$; M.W. 651.96; EC No. 240-140-1
    Trypan Blue: [Direct Blue 14]; $C_{34}H_{24}N_6Na_4O_{14}S_4$; F.W. 960.81; EC No. 200-786-7
    Z-VAD-FMK: $C_{22}H_{30}O_7N_3F$; M.W. 467.5
    Trypsin-EDTA solution 0.25%:0.25%, 2.5 g porcine trypsin, 0.2 g EDTA; M.W. 23.8 kDa; EC No. 3.4.21.4
    N-Acetyl-L-Cysteine: [LNAC; NAC]; $HSCH_2CH(NH-COCH_3)CO_2H$; F.W. 163.19; EC No. 210-498-3
    $_L$-Glutathione reduced: (γ-Glu-Cys-Gyl; CSH); [γ-$_L$-Glutamyl-$_L$-cysteinyl-glycine]; $H_2NCH(CO_2H)CH_2CH_2CONHCH(CH_2SH)CONHCH_2CO_2H$; F.W. 307.32; EC No. 200-725-4

Assays and Kits
    EnzoLyte™ Rh110 Caspase-3 Assay Kit; AnaSpec, San Jose, Calif., USA; Cat No. 71141
    CellTiter® Aqueous One Solution Cell Proliferation Assay; Promega Corporation, Madison, Wis., USA.

RT-PCR Reagents
    QuickPrep micro mRNA Purification Kit; Amersham Pharmacia Biotech; Cat. No. 27-9255-01; Buckinghamshire, UK.
    Ready-To-Go™ You-Prime First-Strand Beads; Amersham Pharmacia Biotech; Cat. No. 27-9261-01; Buckinghamshire, UK.

puReTaq™ Ready-To-Go™ PCR Beads; Amersham Biosciences; Cat. No. 27-9558-01; Piscataway, N.J. USA.

BenchTop 100 bp DNA Ladder; Promega Corporation, Madison, Wis., USA; Cat. No. G8291.

Trackit™ 100 bp DNA Ladder: 0.1 µg/µl; Invitrogen; Cat. No. 10488-058; Paisley, UK.

Agarose 1 Biotechnology Grade; Amresco, Solon, Ohio, USA; Product No. 0710-500G

Ethidium Bromide Fluorescence λ ex 530 nm; λ em 600 nm; [3,8-Diamino-5-ethyl-6-phenylphenanthridinium bromide]; $C_{21}H_{20}BrN_3$; F.W. 394.32; EC No. 1239-45-8; Appligene Oncor, Graffenstaden, Germany.

DAPI: [4',6-Diamidino-2-phenylIndole,dilactate]; $C_{22}H_{27}N_5O_6$; F.W. 457.48 Pd(N)$_6$ Sodium salt; Amersham Pharmacia, NJ. USA; Cat No. 27-2166-01

Primers for RT-PCR: All primer sequences obtained from Alta Biosciences University of Birmingham, UK.

siRNA Reagents

Lipofectamine™ 2000

3:1 (w/w) liposome formulation of the polycationic lipid 2,3-dioleyloxy-N-[2(sperminecarboxamido)ethyl]-M, N-dimethyl-1-propanaminium trifluoroacetate (DOSPA), and the neutral lipid dioleoyl phosphatidylethanolamine (DOPE) in membrane filtered water. Invitrogen, Paisley, UK; Cat No. 11668-019

DNase-, RNase-protease-free Water DEPC treated. Dihydrogen oxide $H_2O$ $M_r$, 18.02 filtered 0.2 µM membrane. EC No. 231-791-2; BioChemika, Fluka, Poole, UK.

RNase Removing Solution Biotechnology Grade; Amresco, Solon, Ohio. USA; Cat No. 6440

OptiMem1 Media; Invitrogen. Paisley, UK; Cat No. 31985-062 siControl RISC-Free siRNA; Dharmacon Inc. Boulder, Colo. USA; Cat No. D-001220-01-20 siControl Non-Targeting siRNA #1; Dharmacon Inc. Boulder, Colo. USA; Cat No. D-001210-01-20 siControl Tox Transfection Control; Dharmacon Inc. Boulder, Colo. USA; Cat No. D-001500-01-20

Individual siRNA Primer Sequences; Dharmacon Inc, Boulder, Colo. USA.

Cell Lines

A. SK-HEP-1 Cells; ECACC (European Collection of Cell Cultures); No. 91091816

Cell Line Name

SK-HEP-1 Human liver adenocarcinoma

Cell Line Description

Derived from an ascites sample from a 52 year old male suffering from adenocarcinoma of the liver. The cells have now been shown to be endothelial in origin (In Vitro 1992; 28A:136).

Species: Human. Tissue: Liver. Morphology: Endothelial

Sub Culture Routine

Split sub-confluent cultures (70-80%) 1:2 to 1:4 i.e. seeding at 2-4×10,000 cells/cm² using 0.25% trypsin or trypsin/EDTA; 5% $CO_2$; 37° C.

Karyotype: Hyperdiploid to hypotriploid

B. U937 (monocytes)—Purchased from ECACC and cultured under known standard conditions.

C. Jurkat (T-cells)—T-lymphocyte leukemic cell line, purchased from ECACC and cultured under known, standard conditions.

Gene Accession

Heme Oxygenase-1 (decyclizing) Human EC 1.14.99.3
    Reaction: heme+$3AH_2$+$3O_2$=biliverdin+$Fe^{2+}$+CO+$3A$+$3H_2O$ Swiss-Prot: P09601 Gene Name: HMOX1 Location: Microsomal Sequence Information Length 288 AA. M.W. 32819 Da. Chromosome 22q12

Heat Shock 70 kDa Human
    Swiss-Prot: P17066 Gene Name: HSPA6 Location: Cytosolic Sequence Information Length 643AA. M.W. 71028 Da. Chromosome 1q23

Transcription regulator protein BACH1 Human
    Swiss-Prot: 014867 Gene Name: BACH-1 Location: Nucleus Sequence Information Length 736 M. M.W. 81958 Da. Chromosome 21q22.11

78 kDA glucose-regulated protein Human
    Swiss-Prot: P11021 Gene Name: HSPA5:GRP78 Location: Endoplasmic reticulum.
    Sequence Information Length 654 M. M.W. 72333 Da. Chromosome 9q33-q34.1

Heat-shock protein beta-1 Human
    Swiss-Prot: P04792 Gene Name: HSP27 Location: Cytoplasm, translocates to nucleus during heat-shock.
    Sequence Information Length 205AA M.W. 22783 Da. Chromosome 7q11.23

Heat shock protein HSP 90-alpha Human
    Swiss-Prot: P07900 Gene Name: HSP90A Location: Cytoplasm Sequence Information Length 731M. M.W. 84529 Da. Chromosome 14q32.33

Heat shock protein HSP 90-beta Human
    Swiss-Prot: P08238 Gene Name: HSP90B Location: Cytoplasm Sequence Information Length 723M. M.W. 83133 Da. Chromosome 6q12

Beta-actin, cytoplasmic 1 Human
    Swiss-Prot: P60709 Gene Name: ACTB Location: Cytoplasm Sequence Information Length 375M. M.W. 41737 Da. Chromosome 7q22.1

94 kDa Glucose-regulated protein Human
    Swiss-Prot: P14625 Gene Name: GRP94 Location: Endoplasmic reticulum
    Sequence Information Length 803AA. M.W. 92469 Da. Chromosome 12q23.3

| | RT-PCR Primer Sequences | |
|---|---|---|
| | Sense Primer | Antisense Primer |
| β-actin | TGC-TAT-CCC-TGT-ACG-CCT-CT | AGT-ACT-TGC-GCT-CAG-GAG-GA |
| Hsp 27 | ATG-GCG-TGG-TGG-AGA-TCA-CC | CAA-AAG-AAC-ACA-CAG-GTC-GC |
| HO-1 | CAG-GCA-GAG-AAT-GCT-GAG-TTC | GCT-TCA-CAT-AGC-GCT-GCA |
| Hsp 70 | TTC-CGT-TTC-CAG-CCC-CCA-ATC | CGT-TCA-GCC-CCG-CGA-TGA-CA |

-continued

RT-PCR Primer Sequences

| | Sense Primer | Antisense Primer |
|---|---|---|
| Hsp 90β | AGA-AGG-TTG-AGA-AGG-TGA-CAA | AAG-AGT-GAG-GGA-ATG-GG |
| grp 78 | GAT-AAT-CAA-CCA-ACT-GTT-AC | GTA-TCC-TCT-TCA-CCA-GTT-GG |
| gp 96 | TGC-CAA-GGA-AGG-AGT-GAA-GT | GTT-GCC-AGA-CCA-TCC-GTA-CT |
| BACH-1 | GGA-CAC-TCC-TTG-CCA-AAT-GCA | TGA-CCT-GGT-TCT-GGG-CTC-TCA |

Primer Sequences Used for RT-PCR.

DNA sequences are indicated from 5' to 3' terminus according to convention. Hsp and grp 78 primers from Wang et al. (1999).

HO-1, gp 96, β-actin and BACH-1 primers designed from gene sequences obtained from the NCBI website, (http://www.ncbi.nlm.nih.gov/).

Primers were designed using Primer 3 software (http://www-qenome.wi.mit.edu/cqi-bin/primer/primer3_www.cgi).

Experimental Methods

The methods used for cell preparation and the various tests are set forth in detail below. The reagents, including assays, kits, and cell lines are described above.

Cell Lines

The SK-HEP-1 (ECACC No. 91091816) is a human liver adenocarcinoma cell line. It is derived from an ascites sample from a 52 year old male human suffering from adenocarcinoma of the liver. The cells have now been shown to be endothelial in origin. SK-HEP-1 cells are very sensitive to homocysteine. Jurkat (T-cells) and U937 (monocytes) cell lines were also used. Jurkat and U937 cells are more resistant to homocysteine than SK-HEP-1 cells, but do demonstrate adverse effects when exposed to homocysteine.

Preparation of Cell Culture Media

Megacell MEM media was supplemented with 3% serum (Fetalclone®1) and 200 mM L-glutamine. Aliquots (2 ml) were regularly transferred to a 24-well plate and examined under a light microscope for infections and integrity of the culture media.

Cell Culture

Cells were subcultured 1.2 in culture flasks or seeded into various plates as required for experimental use. For passaging of SK-HEP-1, the medium was removed and the cells were washed with serum free medium. After addition of 1 ml or 2 ml of trypsin/EDTA 0.4% solution per 25 $cm^2$ or 75 $cm^2$ flask, respectively, the trypsin was removed after 90 seconds. The digestion was stopped after a further 3 minutes by the addition of 5 ml of fresh complete medium. For experimental use, cells between passage three and fifteen were grown in a monolayer until approx. 90% confluent in 6-, 12-, 24-, 48-, or 96-well plates. For siRNA experiments, cells between passage three and ten were grown until approximately 60-70% confluence was reached in 6-, 12-, 24-, or 48-well plates. The cells were allowed to adhere to the plastic surface of the culture vessels for a period of 24 hours prior to experimentation. Cells were grown at 37° C. in a 5% $CO_2$ humidified Heracell incubator.

Determination of Cell Counts and Viability

Routine evaluation of the quality and growth rate of cultured SK-HEP-1 cells was accomplished by use of an inverted phase-contrast microscope at 100× magnification. Endothelial cells display "cobblestone" morphology at confluence. After prolonged maintenance at full confluence, these cells may acquire a 'sprouting' phenotype and infiltrate under other cells. Characteristics of endothelial cells include a flat irregular shape, multiple small vesicles, and pleiomorphic oval nuclei and are approximately 10-20 μm in diameter.

Trypan Blue Exclusion Test of Viability

Regular cell counts were performed and cells were stained with Trypan Blue to determine viability and cell counts. Cells suspended in media were diluted 1:1 with Trypan Blue and incubated for 20 minutes. A cell count was performed using 20 μl of this suspension with a haemocytometer according to the manufacturer's instructions.

Freezing, Storage and Thawing of SK-HEP-1 Cells

For long-term storage, confluent SK-HEP-1 cells were detached with trypsin/EDTA 0.4% solution. Cells were transferred to a centrifuge tube and centrifuged at 218 g for 3 minutes. The culture media was removed and the cell pellet was resuspended in 1.0 ml of freeze media (complete Mega-Cell media supplemented with 10% [v/v] sterile DMSO). The cell suspension was transferred to cryovials and frozen immediately at −20° C. for 24 hours, then at −80° C. for 7 days and then transferred to −96° C. in vapour phase liquid nitrogen. This procedure was performed in order to ensure gradual freezing of the cells to avoid ice-crystal formation within the cell structure. For thawing of cells, SK-HEP-1 cells were warmed quickly in a 37° C. water bath and the cell suspension was immediately transferred to a 25 $cm^2$ cell culture flask containing 9 ml fresh complete MegaCell MEM media. Cells were grown at 37° C. in a 5% $CO_2$ humidified Heracell incubator.

Sterilization of Equipment

Filter units containing 0.2 μm filters were autoclaved for filter sterilization of all reagents used under experimental conditions in culture media.

Cell Treatments

Cells were plated on a 96-well plate at approximately ±5000 cells per well and cultured for 24 hours. Then, subconfluent cells were exposed to test treatments for times indicated. Media was removed from test wells and replaced with 100 μl phenol-red free media containing various concentrations of test compounds. Plates were incubated for either 2 hours or 24 hours.

MTS Assay

MTS® assay is a standard measure of cell activity. The CellTiter 96® Aqueous One Solution Cell Proliferation Assay was used according to the manufacturer's instructions. Reduction of the MS tetrazolium compound to formazan was detected by color development at 490 nm using a Bio-Tek Synergy H.T. Multi-Detection Microplate Reader, running KC-4 v 3.4 software. After treatment, all media was removed and 100 μl of fresh media was added to each well. 20 μl of the CellTiter 96® solution was added to each test well, and the plate was further incubated for 3 hours.

Gene Expression Experiments

Cells were plated into 6-, 12-, or 24-well cell culture clusters, at $2\times10^3$, $2\times10^5$, or $1\times10^5$ cells per well and incubated until 90% confluent. Treatments were applied as above.

Following incubation, cells were subjected to mRNA extraction followed by cDNA synthesis for each sample under test. Polymerase chain reaction cDNA templates were prepared for simplex PCR protocol. PCR products were then visualized using a UV Transilluminator and images captured using a Kodak ID gel imaging system. Densitometry and statistical analysis was then performed on each gene expression band image using PSP® v 10.0 running under Windows XP®.

Preparation of mRNA from Cell Cultures mRNA extraction was performed using the Quickprep micro mRNA Purification Kit. Following incubation of cells post-treatment, the media was removed from the cells, adherent cells were re-suspended in 0.4 ml extraction buffer and 0.8 ml elution buffer at 65° C. was added.

Cell suspension was mixed and transferred to a 1 ml microcentrifuge tube. For each sample, 1 ml of oligo(dt)-cellulose was added to a separate microcentrifuge tube. The cell suspension and oligo(dt)-cellulose were centrifuged for 2 minutes at 15,130 g. Supernatant from the oligo(dt)-cellulose was removed and discarded.

Subsequently, 1 ml of cleared homogenate from cell suspensions was added to the pelleted oligo(dt)-cellulose. The sample was re-suspended by inversion for 3 minutes and further mixed in a WhirliMixer for 30 seconds. This mixing step allows binding to occur between the poly-A-tail of the mRNA and the T bases on the oligo-(dt)-cellulose. The oligo(dt)-cellulose was pelleted by centrifugation at 15,130 g for 10 seconds. The supernatant was then discarded.

Each sample was further re-suspended in 1 ml of HIGH salt buffer, the oligo(dt)-cellulose containing cell sample was pelleted by centrifugation at 15,130 g for 10 seconds.

This HIGH salt washing step was carried out a further four times to remove cell debris.

Each sample was then re-suspended in 1 ml LOW salt buffer, and oligo(dt)-cellulose pelleted by centrifugation at 15,130 g for 10 seconds. The supernatant was discarded. This LOW salt washing step was carried out three times in total.

Each sample was then re-suspended in 0.5 ml LOW salt buffer and the slurry transferred to a clean microcentrifuge tube containing a spin column. Samples were centrifuged at 15,130 g for 5 seconds. The eluant was discarded and 0.5 ml LOW salt buffer was carefully added to the spin column. Samples were centrifuged at 15,130 g for 5 seconds. This final step was repeated three times in total.

The spin columns were transferred to clean microcentrifuge tubes. Pre-warmed elution buffer (0.2 ml) at 65° C. was added to the spin column. Samples were further centrifuged at 15,130 g for 5 seconds. This step elutes the mRNA from the oligo(dt)-cellulose into the microcentrifuge tube. The microcentrifuge tubes were then incubated at 65° C. for ten minutes and then placed on ice to preserve the integrity of the mRNA and to prevent base pairing of the mRNA.

cDNA Synthesis

A reaction mixture was prepared in individual microcentrifuge tubes containing 2 cDNA synthesis beads, 32 μl of the mRNA solution and 1 μl of $pd(N)_6$. This mixture was incubated at 37° C. in a water bath for 60 minutes. After incubation, 27 μl of RNase-free DEPC treated water was added to each tube to make a total volume 60 μl. cDNA samples were prepared in duplicate. Sample 1 was used immediately in RT-PCR protocol. Sample 2 was prepared for qPCR protocol by the addition of 150 μl of 95% ice-cold ethanol and stored at −20° C.

Polymerase Chain Reaction

Microcentrifuge tubes from puReTaq™Ready-To-Go™ PCR Beads containing one PCR bead were labeled for each sample required. Added to the PCR bead were 17 μl of RNase-free DEPC treated water, 1 μl sense primer, 1 μl anti-sense primer and 5 μl of the cDNA solution. RT-PCR conditions were as follows: Hsp70 and β-actin, pre-treatment step, 94° C. for 1 minute, followed by denaturing at 92° C. for 1 minute, annealing at 60° C. for 1 minute and extension at 72° C. for 1 minute. Total cycles, 30, post-treatment was then carried out at 72° C. for 10 minutes. For Hsp32, pre-treatment step, 95° C. for 2 minutes, followed by denaturing at 94° C. for 30 seconds, annealing at 58° C. for 1 minute and extension at 72° C. for 1 minute. Total cycles 45, post treatment was then carried out at 72° C. for 10 minutes. Following RT-PCR, samples were stored at −20° C.

Gel Electrophoresis of RT-PCR Products

Agarose (0.56 g) and 0.56 ml TAE buffer (50×) was added to 27.44 ml ddH₂O. The solution was brought to boiling point for 40 seconds in a microwave. Then, 10 μl ethidium bromide (concentration 1 mg/ml) was added and the solution swirled to mix. Ethidium bromide intercalates with RNA and therefore allows visualization of the bands under UV light. The gel solution was immediately poured into a casting chamber of the electrophoresis kit containing 8-well combs. The gel was allowed to set at room temperature for 30 minutes. The combs were then removed and 100 ml of agarose running buffer was poured into the casting chamber.

Amplification products were separated on a 1.8% agarose gel (m/v) in TAE buffer. The size of the PCR products was determined by comparison to DNA fragments of a well-defined size; therefore, 5 µl of the DNA Ladder was carefully pipetted into the first well of the gel. Successive 10 µl of each PCR sample was then pipetted into subsequent wells on the agarose gel. The gel was connected to the Power Pack and run at 100V for 30 minutes.

Gels were visualised on a UV Transilluminator. Photographs were stored using a Kodak Digital camera system fitted with a UV filter set connected to a PC. Images were then transferred to the Kodak ID gel imaging system. Densitometry was performed on each gene expression band using PSP™ v10 running under Windows XP®.

Caspase-3 Activity (Apoptosis Assay)

Caspase 3 is activated when cells undergo apoptosis. Caspase-3 assay is a standard for apoptosis assay. Homocysteine is a known inducer of apoptosis. Cells were cultured in 96-well plates for 24 hours and then treated with reagents under test conditions. Cytotoxic agents, $H_2O_2$ and etoposide were added to negative control wells. The assay was performed according to the manufacturer's protocol, as follows: Cells were re-suspended in 100 µl of clear media and 50 µl of Caspase-3 substrate solution was immediately added to each test well. Plates were incubated at 37° C. for 60 minutes and formation of free 7-amino-4-trifluoro-methylcoumarin (AFC) was acquired by fluorescence measurement at 496/520 nm by Microplate reader.

Propidium Iodide

Assay Necrosis Assay

Propidium iodide is a standard assay for necrosis. $H_2O_2$ is a known inducer of necrosis. Cells were cultured in 96-well plates for 24 hours and then treated with reagents under test conditions. Cytotoxic agents, $H_2O_2$ and etoposide were added to negative control wells. Cells were re-suspended in 50 µl of clear media and 50 µl of 5 µg/ml propidium iodide solution was added under red-light conditions as the propidium iodide is light sensitive. Plates were incubated at 37° C. for 20 minutes and then absorbance was measured at $\lambda ex$ 535 nm/$\lambda em$ 617 nm by a Microplate reader.

RNA Interference RNAi siRNAs for human HO-1 were synthesised in 2'-deprotected, duplexed, desalted and purified form by Dharmacon Research Inc., published sequences from Zhang et al., (Zhang, Shan et al. 2004). Human Hsp70 primers were from proprietary sequences, and all control non-targeting primer sequences were also synthesised by Dharmacon Research Inc.

First, 200 µl of the 2'-deprotection buffer was added to each 2'-ACE protected, single-stranded complementary RNA strand which was then combined, vortexed and centrifuged. The combined RNA was then incubated at 60° C. for 45 minutes in a dry-heat block. The complexes were then briefly centrifuged for 1-2 seconds and cooled at room temperature for 30 minutes to allow the RNA duplexes to anneal.

Following annealing of the duplexes, 40 µl of the 10M ammonium acetate and 1.5 ml of 100% ethanol was added to 400 µl of siRNA duplex solution and vortexed. The solution was placed at −20° C. for >16 hours or at −70° C. for 2 hours. Following freezing, the solution was centrifuged at 14000 g for 30 minutes at 4° C., then the supernatant was carefully pipetted away from the pellet. The pellet was then rinsed with 200 µl of cold 95% ethanol. The sample was finally dried under vacuum and then re-suspended in 1×siRNA Universal buffer and stored in small aliquots at −20° C. until used.

Transfection was optimised using a standard siControl Tox protocol. All transfection experiments included non-targeted siRNA.

Stock solutions of 2 µM siRNA were removed from a −20° C. freezer 30 minutes before transfection experiments. For triplicate transfections in 96-well plate format, the following master mix of reagents was prepared in RNase-free tubes for distribution of 100 µl per well:

Tube 1—17.5 µl of 2 µM siRNA was added to 17.5 µl OptiMEM media. Total volume 35 µl.

Tube 2—4.8 µl Lipofectamine was added to 30.2 µl OptiMEM media. Total volume 35 µl.

The contents of each tube were mixed and incubated at room temperature for 20 minutes. These tubes were then combined, mixed by pipetting and further incubated for 30 minutes at room temperature. Following incubation, 280 µl OptiMEM media was added to the combined solution.

Forward Transfection Protocol: 2 Day Method

Cells were trypsinized and plated into 12- or 96-well plates at cell density of $2 \times 10^5$, then incubated for 24 hours until adherent. Complexed siRNA and transfection agent at 100 nm was added directly to each experimental well. Plates were incubated at 37° C. for 32.5 hours for mRNA gene analysis experiments or 72 hours for protein analysis by Western Blot.

Reverse Transfection Protocol: 1 Day Method

Complexed siRNA and transfection agent was added to each well of either 12- or 96-well plates. Cells were then trypsinized and added directly into each test well at cell density of $2 \times 10^5$. Plates were incubated at 37° C. for 32.5 hours for mRNA gene analysis experiments or 72 hours for protein analysis by Western Blot.

Statistics

GraphPad Prism™ 4.0 running under Microsoft Windows XP®. All calculations n=6. For single variable comparisons, Student's t-test was used. For multiple variable comparisons, data were analysed by one-way ANOVA with Dunnett test performed post-hoc, where data was compared to control data; $p<0.05$ (95% confidence interval) or $p<0.01$ (99% confidence interval) was considered significant.

Results

Figure 1:
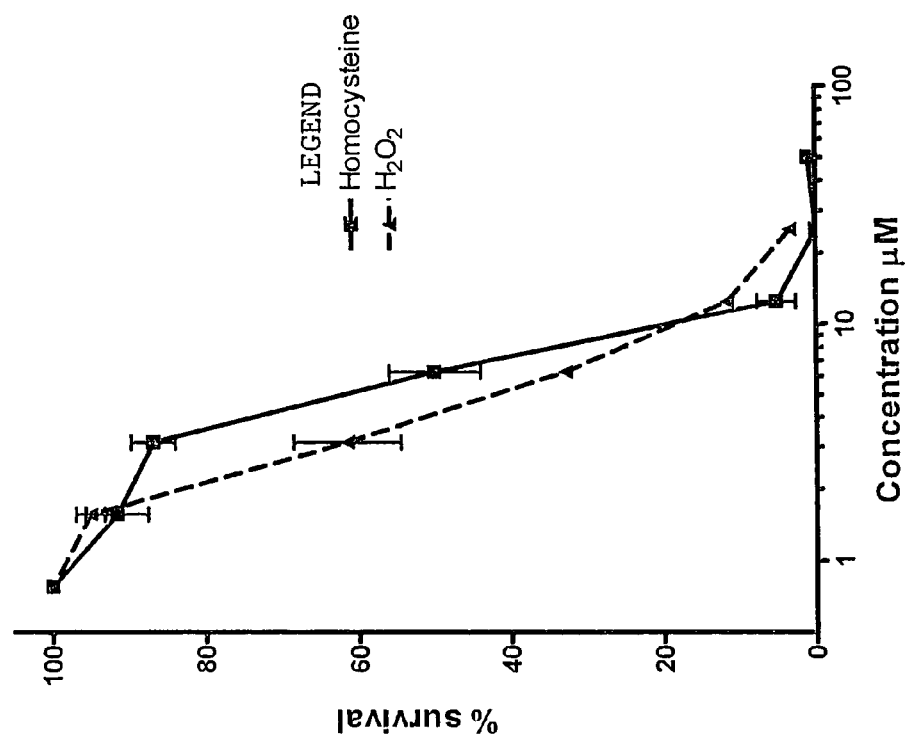
FIG. 1 is a graphic representation showing the effect of homocysteine and $H_2O_2$ on endothelial cell viability

The effects of homocysteine and $H_2O_2$ on endothelial cell viability were assessed first. SK-HEP-1 cells were exposed to increasing concentrations of homocysteine or $H_2O_2$ (range 0-50 µM) for two hours. Cell viability was determined by MTS® assay. Values are shown in FIG. 1 for the means ±SE of six independent samples. FIG. 1 illustrates the effect of homocysteine and $H_2O_2$ on endothelial cell viability. SK-HEP-1 cells were exposed to increasing concentrations of homocysteine or $H_2O_2$ (0-50 µM) for 2 hours. Cell viability was determined by MTS® assay. Values shown are the means ±SE of 6 independent samples. The results showed that concentrations of 3 µm or higher of $H_2O_2$ were sufficient to kill cultured endothelial cells (P<0.001). Greater than 90% (<10% survival) death was achieved by 12.5 µM $H_2O_2$. Concentrations of 5 µM and higher of homocysteine killed cells (p<0.001), and greater than 90% death was achieved by 25 µM homocysteine (FIG. 1).

TABLE 7

| Concentration µM | Homocysteine | Homocysteine | Homocysteine | Homocysteine | Homocysteine | Homocysteine |
|---|---|---|---|---|---|---|
| | n = 6 | | | | | |
| 50 | 0.284276 | −0.43099 | 0.944523 | 1.439709 | 3.255389 | 0.284276 |
| 25 | 1.494729 | −1.31132 | −0.32095 | −0.48601 | 0.504359 | 0.119214 |
| 12.5 | 4.906009 | −0.21091 | 0.394317 | 5.181112 | 3.860618 | 17.12059 |
| 6.25 | 62.01742 | 28.39982 | 38.2485 | 48.6474 | 67.62952 | 55.0298 |
| 3.125 | 95.96514 | 91.61852 | 82.81522 | 78.30353 | 80.94451 | 91.78358 |
| 1.562 | 100.5319 | 102.4026 | 85.18111 | 81.32966 | 81.60476 | 98.82622 |
| 0.781 | 99.76157 | 98.11095 | 102.5676 | 102.4576 | 98.71617 | 98.38605 |

| Concentration µM | $H_2O_2$ | $H_2O_2$ | $H_2O_2$ | $H_2O_2$ | $H_2O_2$ | $H_2O_2$ |
|---|---|---|---|---|---|---|
| 50 | −0.02255 | 0.428443 | −0.24805 | 0.067649 | −0.69904 | 0.473542 |
| 25 | 3.179495 | 3.630486 | 3.630486 | 3.224594 | 3.269693 | 3.585387 |
| 12.5 | 12.42483 | 11.25225 | 10.07967 | 11.83854 | 11.74834 | 12.37973 |
| 6.25 | 32.58418 | 33.89206 | 32.31359 | 35.19994 | 32.53908 | 30.46452 |
| 3.125 | 46.88063 | 52.02194 | 50.62387 | 52.38274 | 82.7345 | 84.53848 |
| 1.562 | 96.44466 | 96.08387 | 96.44466 | 96.67016 | 98.97022 | 85.98165 |
| 0.781 | 99.42121 | 102.4429 | 98.06824 | 98.74472 | 102.3076 | 99.01532 |

The effect of increasing concentrations of NACCbl and GSCbl to protect endothelial cells from the effects of homocysteine was assessed. SK-HEP-1 cells were exposed to increasing concentrations of NACCbl or GSCbl for two (2) hours prior to exposure to 30 µM homocysteine for 24 hours. Cell viability was determined by MTS® assay. Values shown in FIG. 2 are the means ±SE of six (6) independent samples. The level of protection increased with increasing NACCbl and survival was 80% at ≧12.5 µM NACCbl. GSCbl was also effective in protecting cells, but required a higher concentration (>80% survival protection required 50 µM GSCbl). At concentrations below 12.5 µM, the protection provided by NACCbl was significantly greater than that provided by GSCbl (p<0.001).

TABLE 8*

| Concentration NACCbl | NACCbl | NACCbl | NACCbl | NACCbl | NACCbl | NACCbl |
|---|---|---|---|---|---|---|
| 200 | 99.44568 | 100.0554 | 105.0998 | 99.55655 | 96.11974 | 99.8337 |
| 100 | 86.86253 | 88.13747 | 99.61198 | 100.0554 | 96.72949 | 91.18626 |
| 50 | 87.47228 | 89.80045 | 86.6408 | 85.25499 | 90.63194 | 93.12639 |
| 25 | 69.56763 | 79.93348 | 65.2439 | 87.08426 | 79.60089 | 87.41685 |
| 12.5 | 79.93348 | 79.93348 | 70.78714 | 78.10421 | 76.38582 | 93.45898 |
| 6.25 | 63.41463 | 75.55432 | 68.62527 | 72.56098 | 74.72284 | 68.56985 |
| 3.125 | 44.95566 | 55.93126 | 59.70067 | 60.25499 | 53.49224 | 58.75832 |
| 1.78 | 26.44124 | 20.898 | 32.03991 | 31.54102 | 33.75832 | 30.09978 |
| 0 | 131.153 | 111.918 | 108.7583 | 87.41685 | 95.34369 | 93.84702 |

| Concentration GSCbl | GSCbl | GSCbl | GSCbl | GSCbl | GSCbl | GSCbl |
|---|---|---|---|---|---|---|
| 200 | 81.87362 | 76.38582 | 99.6674 | 96.72949 | 92.23947 | 93.18182 |
| 100 | 51.99557 | 87.86031 | 89.91132 | 93.51441 | 108.5366 | 132.2062 |
| 50 | 81.3193 | 103.6585 | 84.31264 | 94.62307 | 102.2727 | 95.50999 |
| 25 | 60.36586 | 65.13304 | 75.77605 | 62.74945 | 69.73393 | 104.102 |
| 12.5 | 56.76275 | 71.50776 | 60.47672 | 56.153 | 51.49668 | 75.49889 |
| 6.25 | 60.42128 | 62.02883 | 64.41241 | 52.32816 | 58.64745 | 57.76053 |
| 3.125 | 30.76497 | 14.74501 | 25.44346 | 23.61419 | 20.898 | 22.56098 |
| 1.78 | 14.13525 | 9.811529 | 6.485587 | 0.997783 | 11.58537 | 9.09091 |
| 0 | 132.2062 | 51.99557 | 87.86031 | 89.91132 | 93.51441 | 108.5366 |

*Varying Concentrations of NACCbl and GSCbl, followed by exposure to 30 µM homocysteine for 24 hours.

Results showed that pre-incubation with ≧2.0 µM of NACCbl protected cells from homocysteine-induced cell death. FIG. 2. Illustrates that NACCbl and GSCbl protect endothelial cells from the effect of homocysteine. SK-HEP-1 cells were exposed to increasing concentrations of NACCbl (■) or GSCbl (▲) for 2 hours prior to exposure to 30 µM homocysteine for 24 hours. Cell viability was determined by MTS® assay. Values shown are the means ±SE of 6 independent samples.

Figure 4:
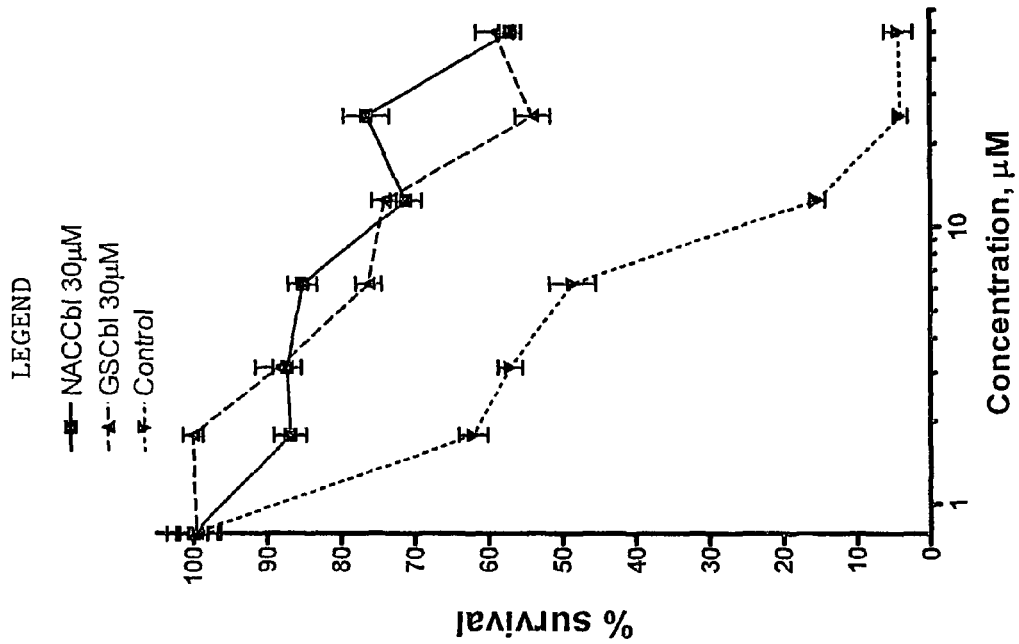
FIG. 4 is a further graphic representation showing that NACCbl and GSCbl protect endothelial cells from the effect of homocysteine.
Figure 3:
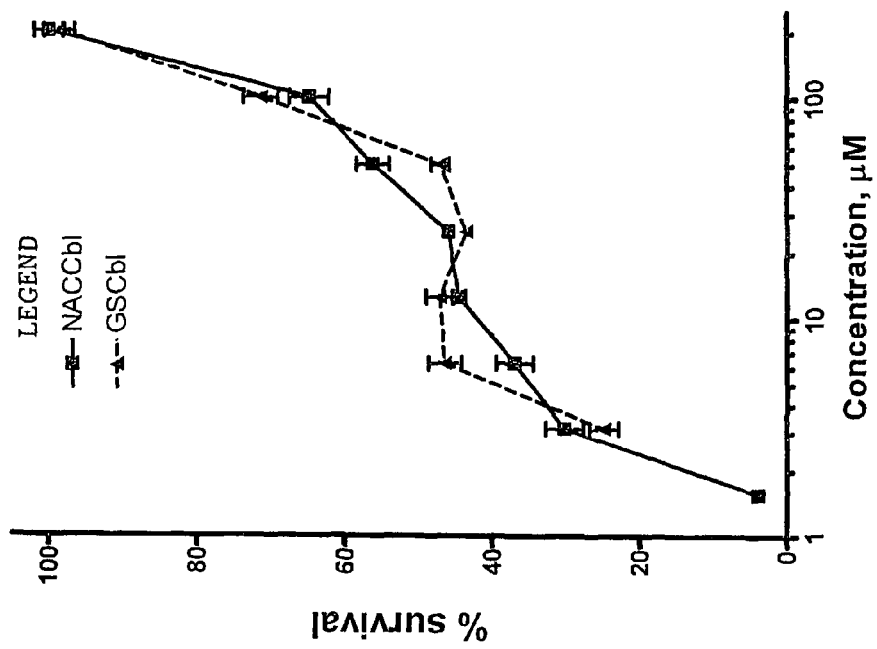
FIG. 3 is a graphic representation showing that NACCbl and GSCbl protect endothelial cells from the effect of $H_2O_2$.

The effect of increasing concentrations of NACCbl and GSCbl to protect endothelial cells from the effect of $H_2O_2$ was assessed. SK-HEP-1 cells were exposed to increasing concentrations of NACCbl or GSCbl for two (2) hours prior to exposure to 25 µM $H_2O_2$ for 24 hours. Cell viability was determined by MTS® assay. Values shown in FIG. 3 are the means ±SE of 6 independent samples. FIG. 3 illustrates that NACCbl and GSCbl protect endothelial cells from the effect of $H_2O_2$. SK-HEP-1 cells were exposed to increasing concentrations of NACCbl (■) or GSCbl (▲) for 2 hours prior to exposure to 25 µM $H_2O_2$ for 24 hours. Cell viability was determined by MTS® assay. Values shown are the means ±SE of 6 independent samples. The results show that preincubation with ≧2.0 µM NACCbl protected cells from $H_2O_2$-induced cell death. There was no difference between the protection afforded by NACCbl and that by GSCbl. Both required 100 µM to achieve >80% survival.

hours. Cell viability was determined by MTS® assay. Data shown in FIG. 4 are representative of means ±SE of 6 independent samples. FIG. 4 illustrates that NACCbl (■) and GSCbl (▲) protect endothelial cells from the effect of homocysteine. Cells were pre-treated with NACCbl or GSCbl (30 µM) for two hours and then exposed to variable concentrations of homocysteine for a further two hours. Cell viability was determined by MTS® assay. Data shown are representative of means ±SE of 6 independent samples. The results

TABLE 9*

| Concentration NACCbl | NACCbl | NACCbl | NACCbl | NACCbl | NACCbl | NACCbl |
|---|---|---|---|---|---|---|
| 200 | 100.7246 | 99.7365 | 101.8445 | 107.3123 | 92.68775 | 97.56258 |
| 100 | 61.5942 | 56.58762 | 70.22398 | 74.37418 | 64.22925 | 61.79184 |
| 50 | 56.65349 | 49.93412 | 60.2108 | 63.24111 | 57.11463 | 49.93412 |
| 25 | 46.90382 | 46.77207 | 45.25692 | 42.68774 | 45.71805 | 48.15547 |
| 12.5 | 45.25692 | 41.69961 | 44.99342 | 45.5863 | 42.22661 | 47.36496 |
| 6.25 | 42.8195 | 42.09486 | 39.39394 | 30.89592 | 27.99737 | 38.4058 |
| 3.125 | 26.8116 | 19.49934 | 35.83663 | 30.50066 | 35.24374 | 33.00395 |
| 1.562 | 4.677207 | 1.844532 | 5.270093 | 1.646904 | 4.347825 | 5.599474 |
| 0 | 128.4585 | 124.1107 | 134.3215 | 115.8103 | 128.4585 | 108.3663 |
| Concentration GSCbl | GSCbl | GSCbl | GSCbl | GSCbl | GSCbl | GSCbl |
| 200 | 94.07115 | 100.0659 | 102.8327 | 93.87352 | 105.5995 | 94.72991 |
| 100 | 64.62451 | 64.62451 | 77.86562 | 71.60738 | 72.59553 | 76.5481 |
| 50 | 42.68774 | 45.71805 | 48.15547 | 46.90382 | 46.77207 | 51.84454 |
| 25 | 41.23847 | 45.5863 | 42.22661 | 45.25692 | 41.69961 | 44.99342 |
| 12.5 | 44.26878 | 54.34783 | 50.52701 | 47.03558 | 44.13702 | 42.09486 |
| 6.25 | 48.68248 | 56.25824 | 45.98156 | 43.34651 | 42.09486 | 41.96311 |
| 3.125 | 20.88274 | 30.89592 | 21.34387 | 26.8116 | 19.49934 | 29.24901 |
| 1.562 | 6.060607 | 1.119894 | −1.58103 | 2.635046 | −0.46113 | −7.83926 |
| 0 | 117.3254 | 129.9737 | 133.5968 | 122.4638 | 120.4875 | 115.1515 |

*Variable concentrations of NACCbl and GSCbl, followed by exposure to 25 µM $H_2O_2$ for 24 hours.

The effect of a constant concentration of NACCbl and GSCbl to protect cells against variable concentrations of homocysteine was assessed. Cells were pre-treated with NACCbl or GSCbl (30 µM) for two hours and then exposed to variable concentrations of homocysteine for a further two show that pre-incubation of cells with 30 µM NACCbl or GSCbl protected cells from homocysteine-induced cell death. There was a decrease in protection as homocysteine concentration increased, but there was still ~60% survival at 50 µM homocysteine.

TABLE 10*

| Variable Concentration Hcy | NACCbl 30 µM | NACCbl 30 µM | NACCbl 30 µM | NACCbl 30 µM | NACCbl 30 µM | NACCbl 30 µM |
|---|---|---|---|---|---|---|
| 200 | −8.4058 | −18.6473 | 11.11111 | 12.75363 | 4.444445 | −1.25604 |
| 100 | 43.28503 | 33.42996 | 40.96619 | 44.92754 | 37.77778 | 41.15942 |
| 50 | 61.5459 | 59.22706 | 55.94203 | 57.68116 | 56.61837 | 50.5314 |
| 25 | 71.0145 | 77.68117 | 86.47344 | 83.96136 | 73.81644 | 66.2802 |
| 12.5 | 66.57005 | 67.24638 | 77.48792 | 72.36715 | 77.00484 | 66.37682 |
| 6.25 | 89.46861 | 80.86957 | 90.62803 | 78.4541 | 85.70049 | 86.18359 |
| 3.125 | 94.87923 | 85.89373 | 87.24638 | 81.35267 | 90.24156 | 84.05798 |
| 1.78 | 88.40581 | 92.85025 | 90.72464 | 88.21256 | 79.03381 | 81.64253 |
| 0.781 | 105.314 | 107.7295 | 97.2947 | 93.33334 | 86.85991 | 109.4686 |
| Variable Concentration Hcy | GSCbl 30 µM | GSCbl 30 µM | GSCbl 30 µM | GSCbl 30 µM | GSCbl 30 µM | GSCbl 30 µM |
| 200 | 5.794027 | 13.84914 | −4.27487 | 6.535942 | −5.86469 | −16.0396 |
| 100 | 8.019773 | 20.95035 | 15.43896 | 28.05157 | 23.2821 | 33.03303 |
| 50 | 66.52534 | 53.91274 | 66.41935 | 56.35047 | 59.6361 | 51.47501 |
| 25 | 64.29959 | 52.85284 | 53.38278 | 46.70552 | 51.26302 | 54.76063 |
| 12.5 | 76.38226 | 66.73732 | 72.56669 | 77.12418 | 75.42837 | 76.80621 |
| 6.25 | 76.38226 | 76.80621 | 77.33616 | 79.03197 | 67.9032 | 80.19784 |

TABLE 10*-continued

| | | | | | | |
|---|---|---|---|---|---|---|
| 3.125 | 88.35894 | 76.9122 | 97.8979 | 89.52482 | 83.58947 | 94.71825 |
| 1.78 | 104.3632 | 94.2943 | 99.6997 | 101.5015 | 100.8656 | 99.27575 |
| 0.781 | 111.4644 | 100.9716 | 92.91645 | 97.47395 | 93.3404 | 100.9716 |

| Variable Concentration Hcy | Control | Control | Control | Control | Control | Control |
|---|---|---|---|---|---|---|
| 200 | −3.784322 | 0.825153 | −0.625979 | 2.361645 | 4.666382 | 3.300612 |
| 100 | 3.385972 | −3.784322 | −5.150093 | 6.032153 | 0.44103 | −0.924741 |
| 50 | 7.09916 | 4.666382 | −3.912363 | 7.09916 | 1.508038 | 8.934416 |
| 25 | 0.825153 | 3.215251 | 3.727415 | 7.568644 | 5.391947 | 2.745767 |
| 12.5 | 10.55627 | 14.90966 | 17.47048 | 15.16574 | 16.27543 | 17.47048 |
| 6.25 | 43.50548 | 62.37018 | 50.80381 | 43.2494 | 41.75558 | 49.69412 |
| 3.125 | 54.517 | 58.35823 | 58.40091 | 50.88917 | 63.01038 | 56.77906 |
| 1.78 | 63.05307 | 55.37061 | 67.5345 | 59.63864 | 67.1077 | 59.42524 |
| 0.781 | 100.441 | 102.2336 | 107.782 | 95.44743 | 98.5631 | 95.53279 |

*Constant concentrations of NACCbl and GSCbl (30 μM), followed by variable concentrations of homocysteine for a further two hours.

Figure 5:
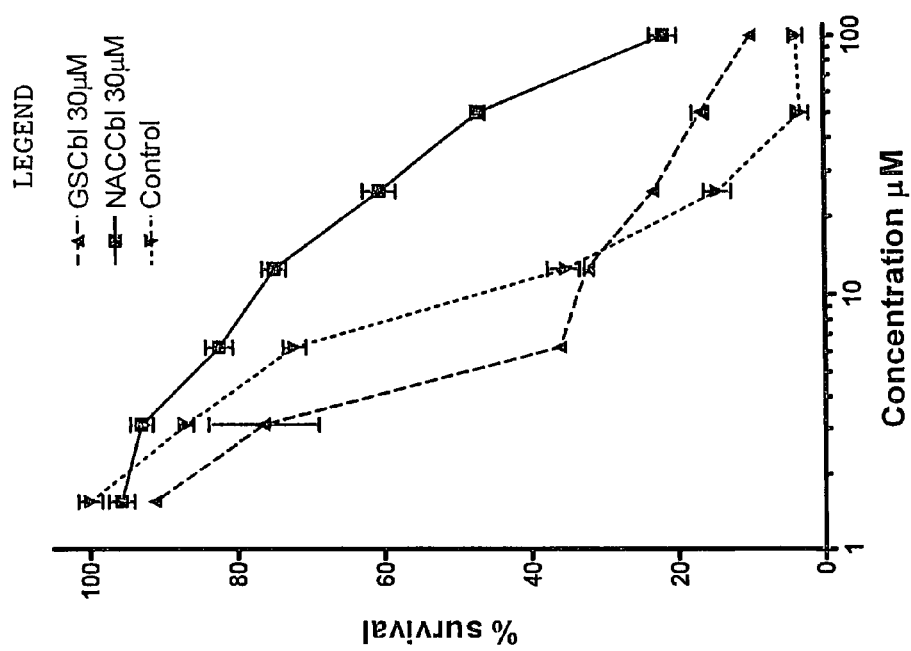
FIG. 5 is a further graphic representation showing that NACCbl and GSCbl protect endothelial cells from the effect of $H_2O_2$.

Protection of endothelial cells by NACCbl (at a constant concentration of 30 μM) was also observed when cells were exposed to variable concentrations of $H_2O_2$, however, the protection decreased below 60% survival above 25 μM $H_2O_2$ (FIG. 5). FIG. 5 illustrates that NACCbl (■) and GSCbl (▲) protect endothelial cells from the effect of $H_2O_2$. Cells were pre-treated with NACCbl or GSCbl (30 μM) for two hours and then exposed to variable concentrations of $H_2O_2$ for a further two hours. Cell viability was determined by MTS® assay. Data shown are representative of means ±SE of 6 independent samples. GSCbl (at a constant concentration of 30 μM) did not provide significant protection above 7.5 μM $H_2O_2$ (also FIG. 5).

TABLE 11*

| | n = 6 | | | | | |
|---|---|---|---|---|---|---|
| $H_2O_2$ Concentration μM | NACCbl 30 μM | NACCbl 30 μM | NACCbl 30 μM | NACCbl 30 μM | NACCbl 30 μM | NACCbl 30 μM |
| 200 | 5.2108 | −0.61582 | 7.153008 | −1.65798 | 1.989578 | 0.663193 |
| 100 | 29.98579 | 23.96968 | 19.56419 | 18.901 | 17.52724 | 20.89057 |
| 50 | 50.21317 | 48.27095 | 44.955 | 45.71293 | 48.17622 | 44.57603 |
| 25 | 67.12459 | 66.74561 | 61.86642 | 56.18191 | 55.3766 | 55.94505 |
| 12.5 | 77.16722 | 76.97774 | 76.59877 | 67.12459 | 77.6883 | 74.13548 |
| 6.25 | 88.20464 | 87.58881 | 82.14117 | 81.57272 | 78.06727 | 77.11985 |
| 3.125 | 88.20464 | 93.17859 | 92.89436 | 99.76315 | 92.42065 | 91.80482 |
| 1.56 | 98.53151 | 91.37849 | 98.72099 | 100.1421 | 89.76788 | 96.11559 |
| 0.781 | 93.46281 | 102.7949 | 99.24207 | 101.3738 | 103.2686 | 95.45239 |
| 0 | 102.9844 | 100.8053 | 103.2212 | 107.9583 | 101.8948 | 98.43676 |

| $H_2O_2$ Concentration μM | GSCbl 30 μM | GSCbl 30 μM | GSCbl 30 μM | GSCbl 30 μM | GSCbl 30 μM | GSCbl 30 μM |
|---|---|---|---|---|---|---|
| 200 | 1.326385 | 7.153008 | 3.60019 | 1.942207 | 5.921364 | 0.757935 |
| 100 | 10.80057 | 12.36381 | 11.5585 | 9.995263 | 6.679299 | 8.526765 |
| 50 | 15.01658 | 20.8432 | 18.94837 | 13.12174 | 15.6324 | 17.62198 |
| 25 | 23.54334 | 26.52771 | 22.92752 | 24.44339 | 22.02748 | 20.41686 |
| 12.5 | 29.7963 | 32.02274 | 36.09664 | 32.40171 | 29.98579 | 33.91758 |
| 6.25 | 36.52297 | 39.7442 | 34.48603 | 34.72288 | 34.86499 | 36.09664 |
| 3.125 | 40.31265 | 91.33112 | 87.3046 | 82.33065 | 79.77262 | 77.59356 |
| 1.56 | 93.55756 | 90.81004 | 92.32591 | 88.25201 | 90.81004 | 91.8522 |
| 0.781 | 96.11559 | 98.38939 | 97.3946 | 98.0578 | 96.02085 | 95.31028 |
| 0 | 99.24207 | 102.2264 | 105.5898 | 103.6002 | 104.0265 | 104.5476 |

| $H_2O_2$ Concentration μM | Control | Control | Control | Control | Control | Control |
|---|---|---|---|---|---|---|
| 200 | 4.263382 | −1.61061 | −0.52108 | −2.17906 | 1.56324 | −1.51587 |
| 100 | 1.326385 | 0.757935 | 4.547607 | 3.458076 | 5.447654 | 6.679299 |
| 50 | 3.837044 | 7.153008 | −1.56324 | 3.60019 | 3.837044 | 2.321175 |
| 25 | 19.42208 | 10.27949 | 13.73757 | 19.75367 | 15.58503 | 8.810989 |
| 12.5 | 34.86499 | 40.31265 | 44.71814 | 30.22264 | 32.49645 | 28.61203 |
| 6.25 | 72.38276 | 73.04596 | 67.17196 | 72.28801 | 78.63572 | 69.58788 |
| 3.125 | 87.92043 | 87.54145 | 83.98862 | 90.81004 | 84.41497 | 87.25723 |
| 1.56 | 93.46281 | 98.29465 | 99.33681 | 101.0422 | 104.6897 | 103.2212 |

TABLE 11*-continued

| | | | n = 6 | | | |
|---|---|---|---|---|---|---|
| 0.781 | 93.46281 | 102.3212 | 96.11559 | 100.8053 | 103.2686 | 101.5632 |
| 0 | 110.2795 | 108.8584 | 109.9479 | 113.6902 | 109.9479 | 114.35354 |

*Constant concentrations of NACCbl at 30 µM, followed by exposure to variable concentrations of $H_2O_2$.

Figure 6:
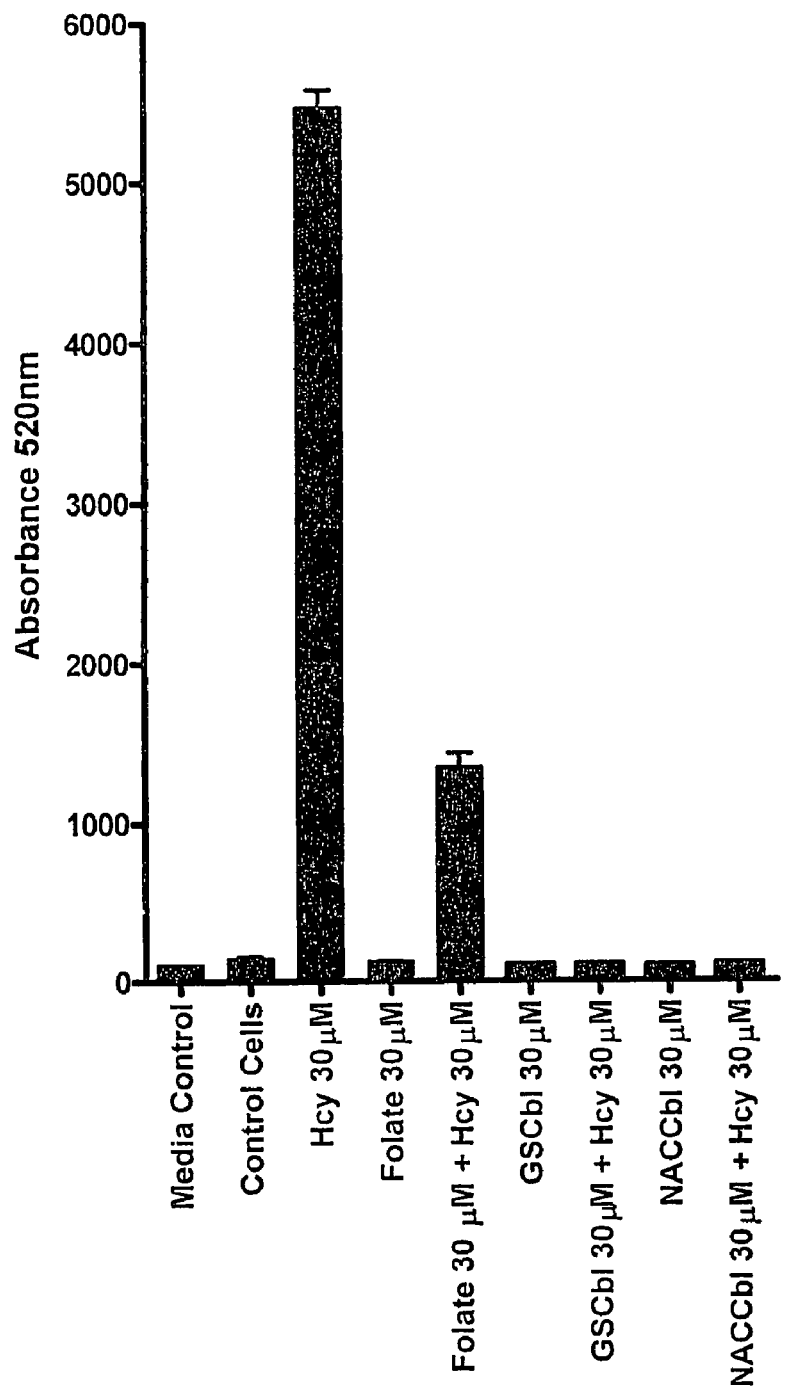
FIG. 6 is a graphic representation showing that NACCbl and GSCbl protect endothelial cells from apoptosis induced by homocysteine.

The effects of NACCbl, GSCbl and folate to protect endothelial cells from apoptosis induced by homocysteine were also assessed. Homocysteine-induced apoptosis in cells was measured by Caspase-3 activity (FIG. 6). FIG. 6 illustrates that NACCbl, GSCbl and folate protect endothelial cells from apoptosis induced by homocysteine. Cells were pre-treated with NACCbl, GSCbl or folate for two hours and then exposed to 0 or 30 µM homocysteine for a further two hours. Cell viability was determined by MTS® assay. Data shown are representative of means ±SE of 6 independent samples. Cells were pretreated with NACCbl, GSCbl or folate (all at 30 µM) for two hours and then exposed to 0 or 30 µM homocysteine for a further two hours. Cell viability was determined by MTS® assay. Data shown in FIG. 6 are representative of means ±SE of 6 independent samples. The results showed that pre-incubation with folate provided partial protection against apoptosis induced by homocysteine, whereas both NACCbl and GSCbl provided total protection.

Figure 7:
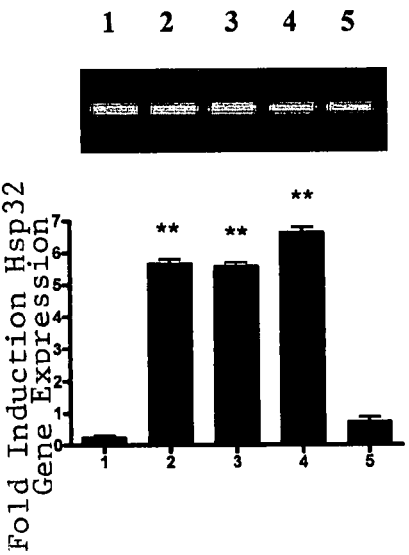
FIG. 7 is a series of plots showing the effect of oxidative stress on Hsp32 and Hsp70 gene expression in SK-HEP-1 Cells.
Figure 7:
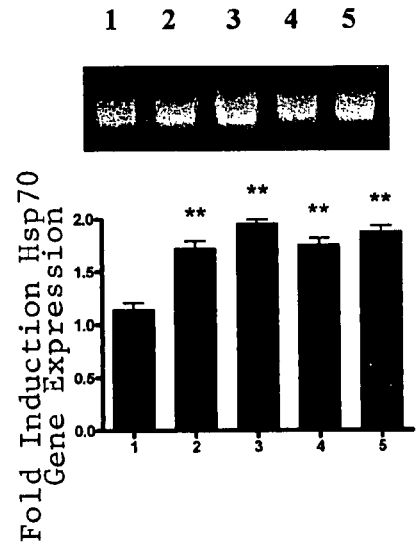
Figure 7:
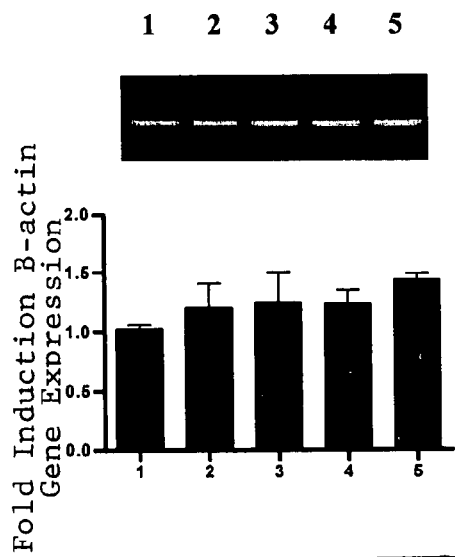
Figure 8:
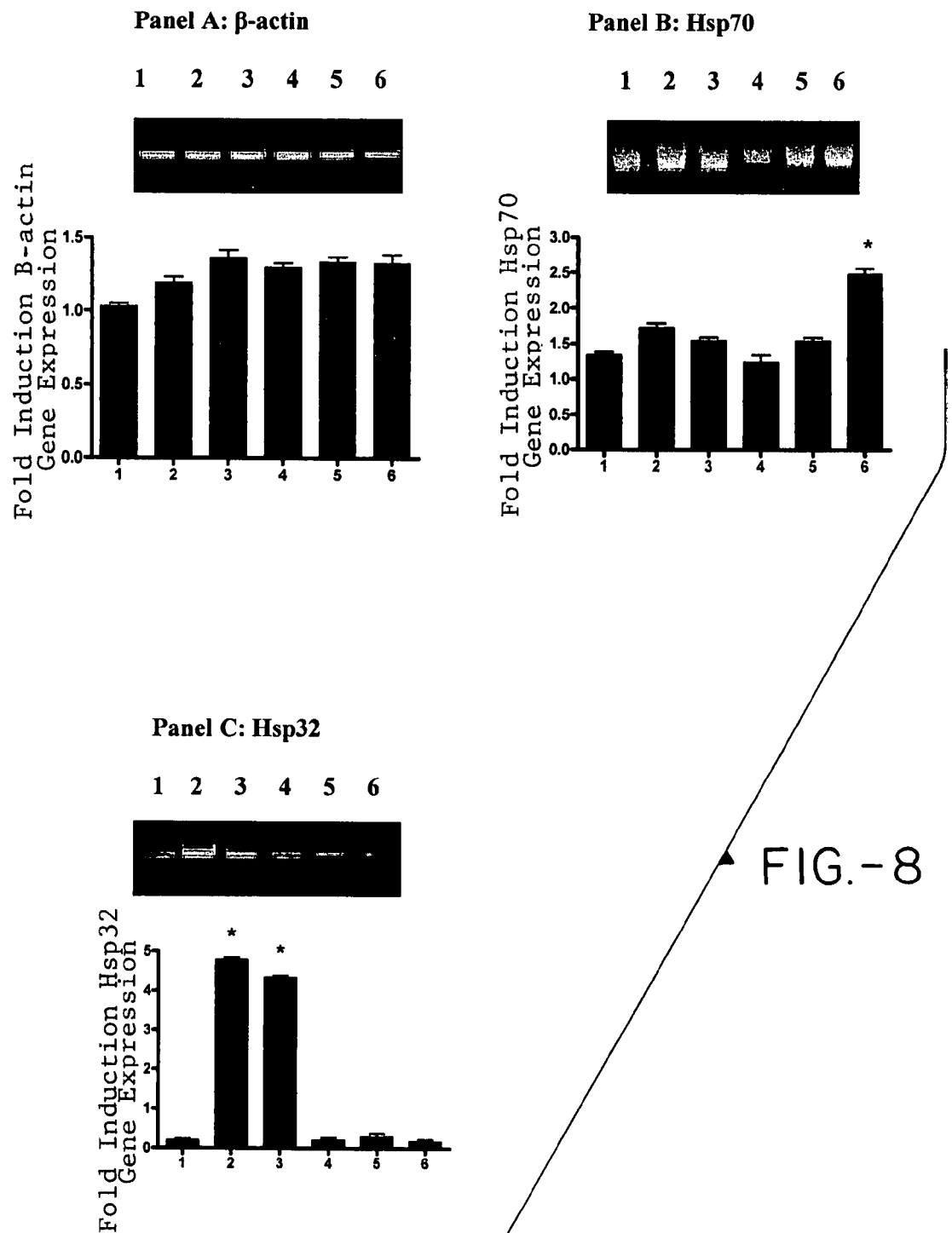
FIG. 8 illustrates a gene expression study for oxidative stress of SK-HEP-1 Cells.

Efforts were made to elicit the mechanism by which NAC-Cbl affords protection to endothelial cells. Experiments were conducted using Hsp32 and Hsp 70 gene expression as the basis for study. Homocysteine is an oxidative stress inducer and as such should induce the expression of heat shock protein (Hsp) Hsp32. FIG. 7 shows the results of oxidative stress on Hsp32 and Hsp 70 gene expression with no treatment, Hcy 30 µM, folate 30 µM, folate 30 µM plus Hcy 30 µM, and heat shock at 42° C. (all treatments for 2 hours). The densitometric data are presented in FIG. 6 as means ±SEM of n=3 separate experiments (p<0.05 or p<0.01, treatment vs. control). The results showed that the Hsp70 gene was expressed in control cells (no treatment), whereas the Hsp32 gene was not (FIG. 7). FIG. 7 illustrates that the effect of oxidative stress on Hsp32 and Hsp70 gene expression in SK-HEP-1 Cells. All panels: 1, no treatment; 2: Hcy 30 µM, 2 hr; 3: folate 30 µM, 2 hr; 4: folate 30 µM, 2 hr+Hcy 30 µM, 2 hr; 5: Heat shock 42° C., 2 hr. The densitometric data are presented as means ±SEM of n=3 separate experiments. * p<0.05 or ** p<0.01, treatment vs. control. An increase in expression of both genes was induced by 30 µM homocysteine, by 30 µM folate and by folate plus homocysteine (both at 30 µM concentration). A 42° C. heat shock increased expression of Hsp70, but not Hsp32, confirming that Hsp32 is specifically induced by oxidative stress. FIG. 8 illustrates a Gene Expression Study: Oxidative stress of SK-HEP-1 Cells. Panel A, B and C: Lane 1 shows the control, no treatment; lane 2: $H_2O_2$ 25 µM, 2 hr; lane 3: folate 30 µM, 2 hr+$H_2O_2$ 25 µM, 1 hr; lane 4: Sn(IX)PP 25 µM, 2 hr; lane 5: Sn(IX)PP 25 µM, 2 hr+folate 30 µM, 2 hr+$H_2O_2$ 25 µM, 1 hr; lane 6: Heat shock 42° C., 2 hr. Panel B shows fold induction difference in β-actin gene expression from Control=1.

Figure 9:
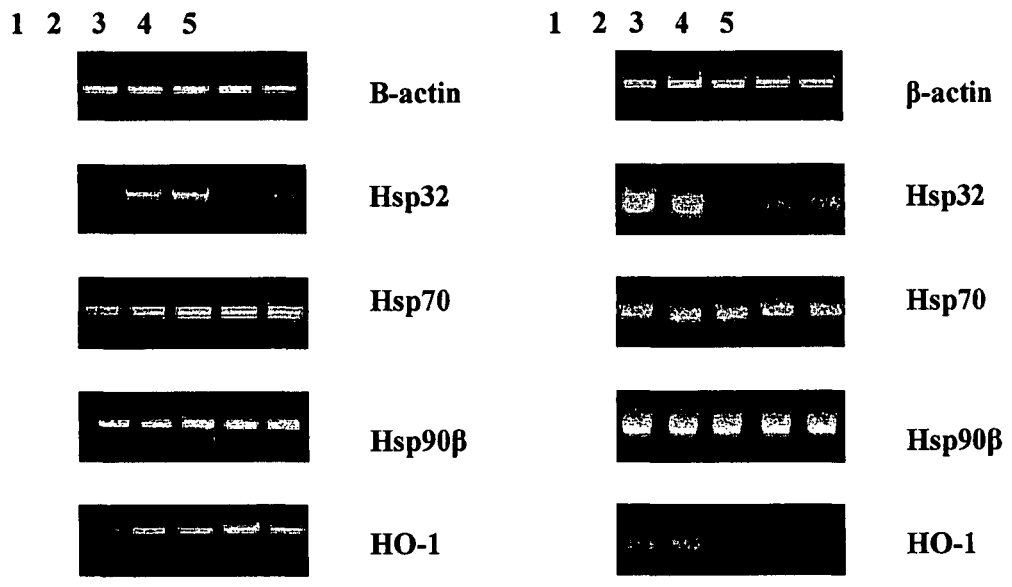
FIG. 9 illustrates Hsp32 gene expression as induced by homocysteine and NACCbl.
Figure 10:
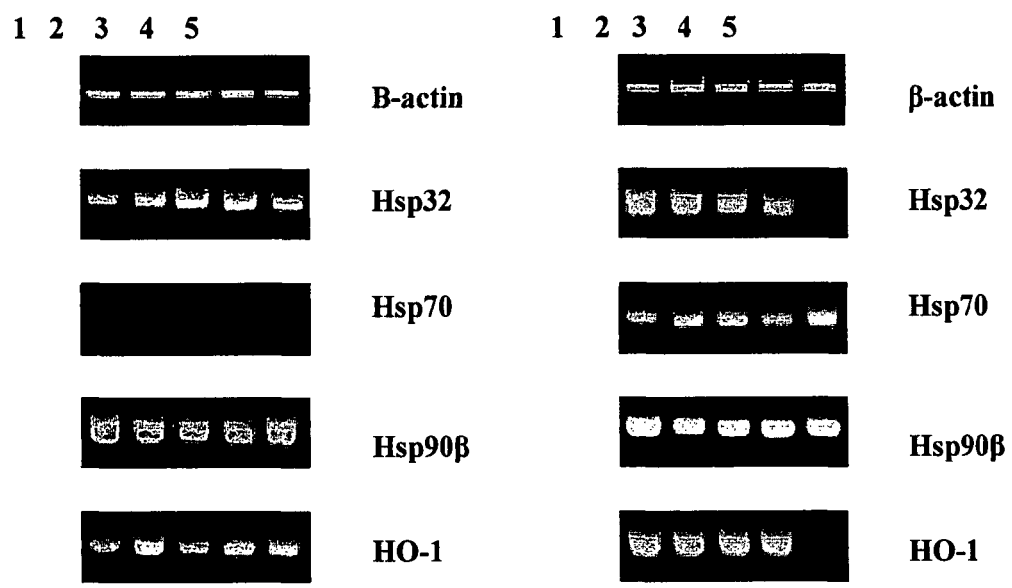
FIG. 10 illustrates Hsp32 gene expression as inhibited by quercitin.

FIG. 9 illustrates that Hsp32 gene expression is induced by homocysteine and NACCbl, and can be inhibited by Sn(IX) protoporphyrin. SK-HEP-1 cells were treated with various compounds prior to PCR. (note HO1=Hsp32). FIG. 9 also shows that the Hsp32 gene can be inhibited by Sn (IX) protoporphyrin (25 µM). Other molecules, including NACCbl and GSCbl, that protect against homocysteine-induced cell death also induce Hsp32 (FIGS. 7, 9 and 10). Quercitin 15 µM inhibits Hsp70 gene expression, but does not inhibit Hsp32 gene expression (FIGS. 9 and 10).

Two alternative approaches were used to determine whether Hsp32 or Hsp70 have a role in the mechanism by which NACCbl protects against homocysteine induced cell death. Hsp32 was inhibited using either Sn (IX) protoporhyrin or using an siRNA which specifically knocks out Hsp32. Hsp70 was inhibited using quercitin or using an siRNA which specifically knocks out Hsp70. In addition, two methods were used to inhibit both Hsp32 and Hsp70: chemically Sn (IX) protoporphyrin plus quercitin was used; and then, directly, a combination of the siRNA for both genes was used simultaneously.

Figure 11:
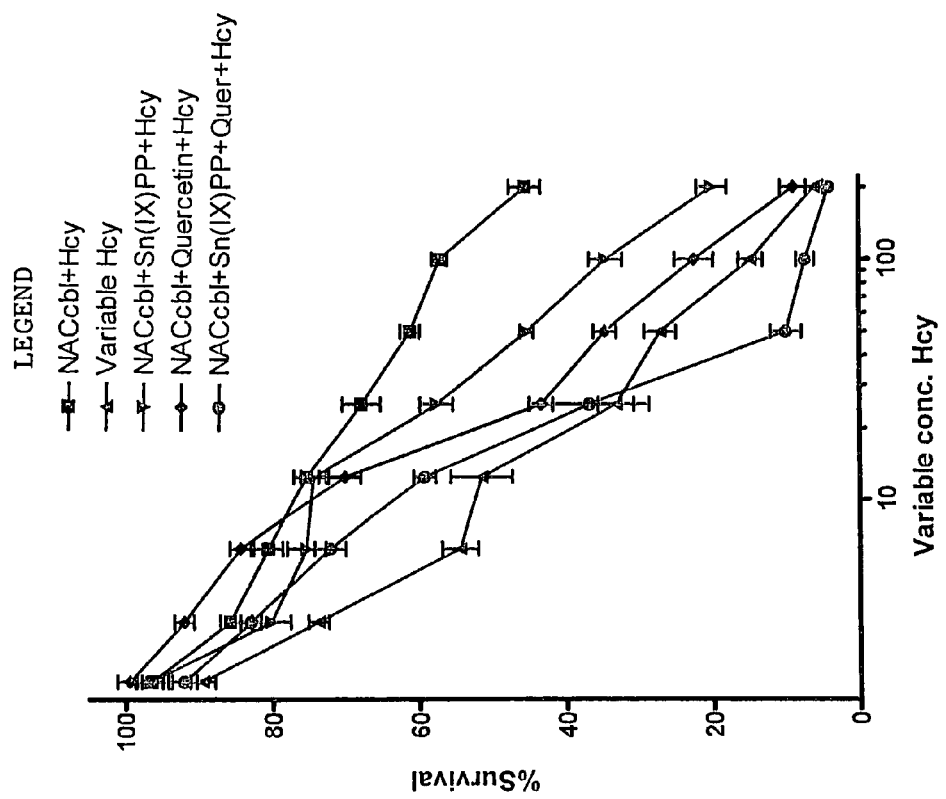
FIG. 11 illustrates that NACCbl protects endothelial cells from the effect of homocysteine via a mechanism involving Hsp70 and Hsp32.
Figure 12:
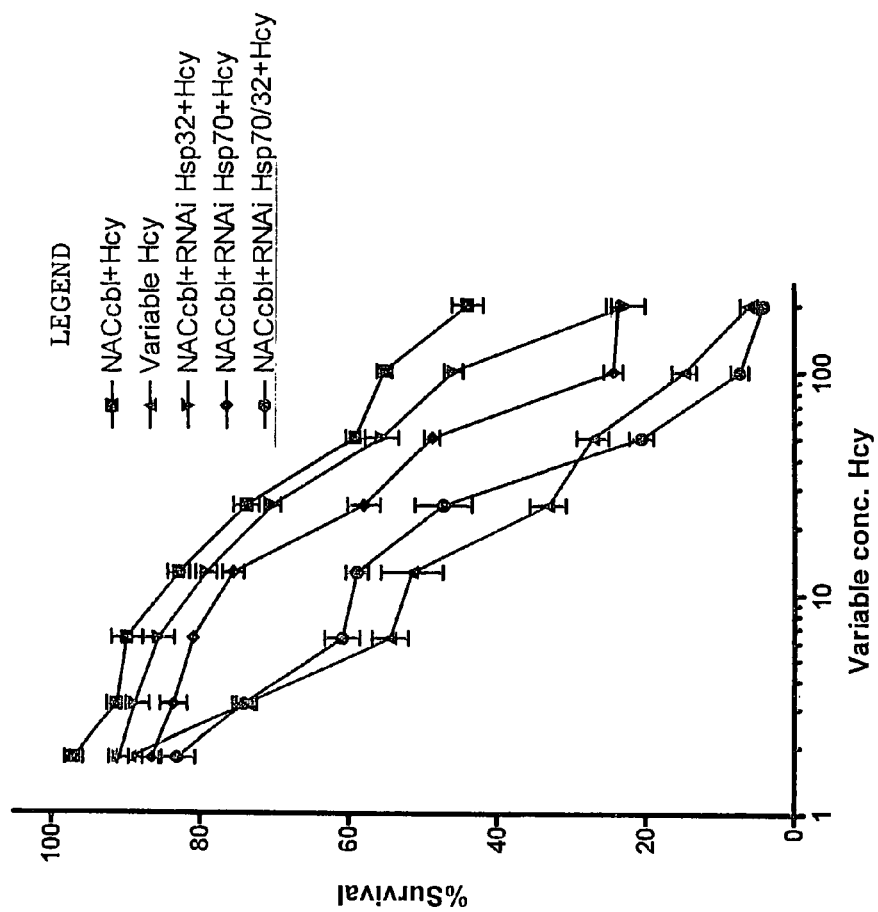
FIG. 12 also illustrates that NACCbl protects endothelial cells from the effect of homocysteine.

In one set of experiments, cells were pre-treated with NAC-Cbl (30 µM) for two hours in the presence or absence of Sn (IX) protoporphyrin or quercitin and then exposed to variable concentrations of homocysteine for a further two hours. Cell viability was determined by MTS® assay. Data shown in FIG. 11 are representative of means ±SE of 6 independent samples. In another set of experiments, cells were pre-treated NACCbl (30 µM) for two (2) hours in the presence or absence of siRNA specific for Hsp32 or Hsp70 and then exposed to variable concentrations of homocysteine for a further two hours. FIG. 11 illustrates that NACCbl protects endothelial cells from the effect of homocysteine via a mechanism involving Hsp70 and Hsp32. Cells were pre-treated with NACCbl (30 µM) for two hours in the presence or absence of Sn(IX) protoporphyrin or quercitin and then exposed to variable concentrations of homocysteine for a further two hours. Cell viability was determined by MTS® assay. Data shown are representative of means ±SE of 6 independent samples. FIG. 12 illustrates NACCbl protects endothelial cells from the effect of homocysteine. Cells were pre-treated NACCbl (30 µM) for two hours in the presence or absence of siRNA specific for Hsp32 or Hsp70 and then exposed to variable concentrations of homocysteine for a further two hours. Cell viability was determined by MTS® assay. Data shown are representative of means ±SE of 6 independent samples. Cell viability was determined by MTS® assay. Data shown are representative of means ±SE of 6 independent samples. The results showed that inhibition of Hsp32 by both methods (chemically and directly) reduced the protection by NACCbl by 10-20% (p<0.001, FIGS. 11 and 12). Inhibition of Hsp70 by both methods (chemically and directly) reduced the protection by NACCbl by 20-40% (p<0.001, FIGS. 11 and 12). Inhibition of both Hsp32 and Hsp70 together by both methods (chemically and directly) totally removed protection by NACCbl (FIGS. 11 and 12).

TABLE 12

(FIG. 11)

| Variable | NACCbl + Hcy (N = 6) | | | | | |
|---|---|---|---|---|---|---|
| Conc. of Hcy | 1 | 2 | 3 | 4 | 5 | 6 |
| 200 | 1.378 | 1.167 | 1.33 | 1.456 | 1.491 | 1.537 |
| 100 | 1.678 | 1.592 | 1.694 | 1.773 | 1.732 | 1.639 |
| 50 | 1.678 | 1.832 | 1.881 | 1.73 | 1.74 | 1.855 |
| 25 | 2.1 | 2.19 | 1.879 | 1.937 | 1.779 | 1.837 |
| 12.5 | 2.21 | 2.11 | 2.045 | 2.065 | 2.101 | 2.324 |
| 6.25 | 2.41 | 2.4 | 2.322 | 2.201 | 2.115 | 2.187 |
| 3.125 | 2.453 | 2.338 | 2.36 | 2.317 | 2.418 | 2.535 |
| 1.78 | 2.647 | 2.551 | 2.789 | 2.89 | 2.549 | 2.611 |
| 0 | 2.885 | 2.698 | 2.821 | 2.771 | 2.691 | 2.7 |

| Variable | Variable Hcy (n = 6) | | | | | |
|---|---|---|---|---|---|---|
| Conc. of Hcy | 1 | 2 | 3 | 4 | 5 | 6 |
| 200 | 0.33 | 0.312 | 0.39 | 0.302 | 0.421 | 0.406 |
| 100 | 0.654 | 0.449 | 0.466 | 0.501 | 0.522 | 0.51 |
| 50 | 0.678 | 0.881 | 0.602 | 0.77 | 0.724 | 0.779 |
| 25 | 0.692 | 0.956 | 0.876 | 0.882 | 0.937 | 0.74 |
| 12.5 | 1.104 | 1.001 | 1.042 | 1.114 | 1.324 | 1.479 |
| 6.25 | 1.304 | 1.406 | 1.227 | 1.176 | 1.15 | 1.119 |
| 3.125 | 1.543 | 1.487 | 1.656 | 1.63 | 1.593 | 1.558 |
| 1.78 | 1.746 | 1.932 | 1.95 | 1.83 | 1.837 | 1.884 |
| 0 | 2.109 | 2.11 | 1.999 | 2.056 | 2.1 | 1.936 |

| Variable | NACCbl + Sn(IX)PP + Hcy (n = 6) | | | | | |
|---|---|---|---|---|---|---|
| Conc. of Hcy | 1 | 2 | 3 | 4 | 5 | 6 |
| 200 | 0.679 | 0.837 | 0.882 | 0.91 | 0.723 | 0.577 |
| 100 | 1.29 | 1.117 | 1.104 | 1.002 | 0.994 | 1.336 |
| 50 | 1.488 | 1.47 | 1.43 | 1.379 | 1.337 | 1.402 |
| 25 | 1.876 | 1.749 | 1.678 | 1.63 | 1.557 | 1.921 |
| 12.5 | 2.123 | 2.301 | 2.244 | 2.221 | 2.109 | 2.008 |
| 6.25 | 2.443 | 2.331 | 2.156 | 2.004 | 2.078 | 2.14 |
| 3.125 | 2.578 | 2.432 | 2.29 | 2.278 | 2.21 | 2.11 |
| 1.78 | 2.567 | 2.69 | 2.733 | 2.779 | 2.821 | 2.879 |
| 0 | 2.6788 | 2.897 | 2.701 | 2.857 | 2.891 | 2.945 |

| Variable | NACCbl + Quercetin + Hcy (n = 6) | | | | | |
|---|---|---|---|---|---|---|
| Conc. of Hcy | 1 | 2 | 3 | 4 | 5 | 6 |
| 200 | 0.573 | 0.423 | 0.444 | 0.301 | 0.567 | 0.583 |
| 100 | 1.111 | 1.678 | 0.732 | 0.883 | 0.891 | 0.693 |
| 50 | 1.021 | 1.247 | 1.207 | 1.197 | 1.177 | 1.022 |
| 25 | 1.478 | 1.501 | 1.376 | 1.321 | 1.297 | 1.25 |
| 12.5 | 2.123 | 2.116 | 2.046 | 2.1 | 2.187 | 1.794 |
| 6.25 | 2.467 | 2.409 | 2.337 | 2.365 | 2.401 | 2.588 |
| 3.125 | 2.765 | 2.631 | 2.661 | 2.589 | 2.603 | 2.509 |
| 1.78 | 2.678 | 2.889 | 2.921 | 2.703 | 2.831 | 2.899 |
| 0 | 2.991 | 2.851 | 2.956 | 2.756 | 2.764 | 2.678 |

| Variable | NACCbl + Sn(IX)PP + Quercetin + Hcy (n = 6) | | | | | |
|---|---|---|---|---|---|---|
| Conc. of Hcy | 1 | 2 | 3 | 4 | 5 | 6 |
| 200 | 0.278 | 0.389 | 0.41 | 0.336 | 0.333 | 0.417 |
| 100 | 0.367 | 0.401 | 0.476 | 0.507 | 0.551 | 0.367 |
| 50 | 0.746 | 0.478 | 0.539 | 0.337 | 0.439 | 0.551 |
| 25 | 1.123 | 1.034 | 0.786 | 1.809 | 1.922 | 0.664 |
| 12.5 | 1.678 | 1.89 | 1.709 | 1.902 | 1.834 | 1.88 |
| 6.25 | 2.123 | 2.39 | 2.167 | 2.117 | 2.17 | 1.963 |
| 3.125 | 2.456 | 2.389 | 2.301 | 2.489 | 2.447 | 2.567 |
| 1.78 | 2.789 | 2.657 | 2.489 | 2.699 | 2.798 | 2.662 |
| 0 | 2.888 | 2.79 | 2.901 | 2.979 | 2.991 | 2.804 |

TABLE 13

(FIG. 12)

| Variable Conc. of Hcy | Mean | SEM |
|---|---|---|
| NACCbl + Hcy | | |
| 200 | 43.9595 | 2.101288 |
| 100 | 55.16888 | 1.013695 |
| 50 | 59.06556 | 1.271858 |
| 25 | 73.75504 | 1.724869 |
| 12.5 | 82.83664 | 1.460632 |
| 6.25 | 89.85452 | 2.128654 |
| 3.125 | 91.34142 | 1.305542 |
| 1.78 | 97.04544 | 1.198051 |
| 0 | 100 | 0.929276 |
| Variable Hcy | | |
| 200 | 6.114708 | 1.68879 |
| 100 | 14.81961 | 1.644149 |
| 50 | 27.14154 | 2.160151 |
| 25 | 33.14524 | 2.430397 |
| 12.5 | 51.47086 | 4.194286 |
| 6.25 | 54.41258 | 2.442547 |
| 3.125 | 73.70027 | 1.393837 |
| 1.78 | 89.53746 | 1.702477 |
| 0 | 100 | 1.608582 |
| NACCbl + RNAi + Hsp 32 + Hcy | | |
| 200 | 22.71906 | 2.604406 |
| 100 | 45.81881 | 1.243889 |
| 50 | 55.51684 | 2.269596 |
| 25 | 70.24131 | 1.135635 |
| 12.5 | 79.12633 | 1.428551 |
| 6.25 | 85.54007 | 2.120552 |
| 3.125 | 88.81791 | 2.042473 |
| 1.78 | 91.044 | 1.296631 |
| 0 | 100 | 2.045876 |
| NACCbl + RNAi + Hsp 70/32 + Hcy | | |
| 200 | 4.156479 | 0.830308 |
| 100 | 7.328696 | 1.192364 |
| 50 | 20.61939 | 1.645706 |
| 25 | 47.21334 | 3.858868 |
| 12.5 | 58.88659 | 1.501209 |
| 6.25 | 60.86139 | 2.375267 |
| 3.125 | 74.12074 | 1.424911 |
| 1.78 | 83.07944 | 2.454529 |
| 0 | 100 | 1.008469 |
| NACCbl + RNAi + Hsp 70 + Hcy | | |
| 200 | 23.74355 | 0.881615 |
| 100 | 24.32296 | 1.313255 |
| 50 | 48.75299 | 1.06419 |
| 25 | 57.9481 | 2.211338 |
| 12.5 | 75.53218 | 1.459312 |
| 6.25 | 80.8918 | 0.7901 |
| 3.125 | 83.51177 | 1.823074 |
| 1.78 | 86.53482 | 1.290047 |
| 0 | 100 | 1.468781 |

Figure 13:
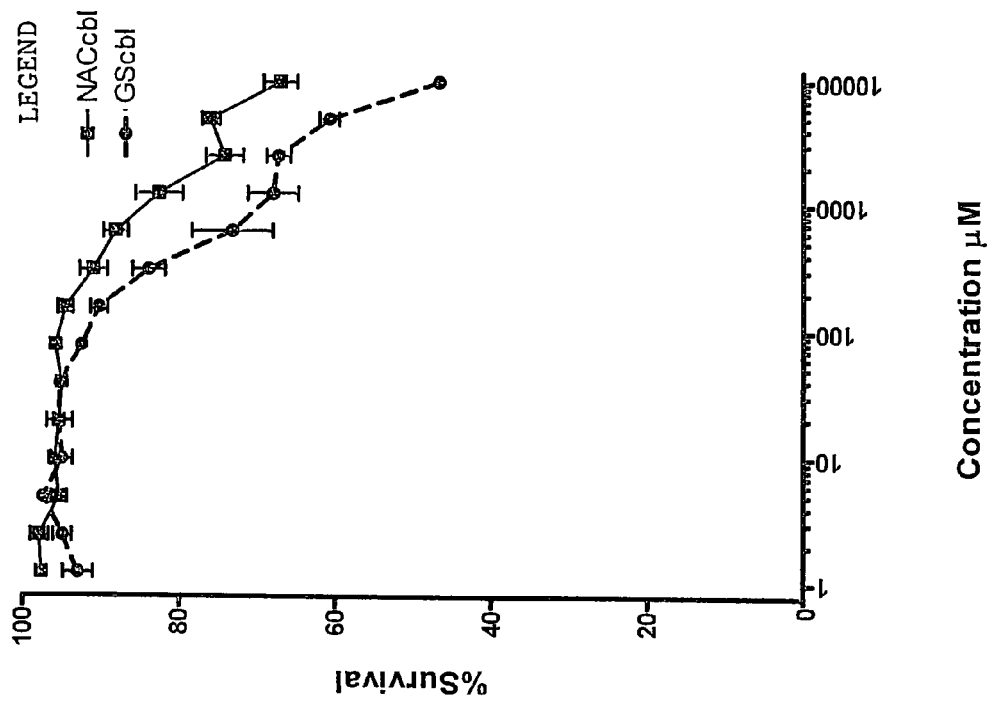
FIG. 13 illustrates the effect of high concentrations of NACCbl and GSCbl on SK-HEP-1 cells.

The concentrations needed for clinical treatments and supplementation may well need to be higher than those used for the cellular experiments described herein. Equally important to the use of thiolatocobalamins to protect endothelial and other cells from the effects of oxidative stress is their safety or lack of a detrimental effect on exposed cells. The effect of high concentrations of NACCbl and GSCbl on SK-HEP-1 cells was evaluated. Cells were exposed to both compounds in increasing concentrations over twenty-four (24) hours. Cell viability was determined by MTS® assay. Data shown in FIG. 13 are representative of means ±SE of 3 independent samples. FIG. 13 illustrates that the effect of high concentrations of NACCbl and GSCbl on SK-HEP-1 cells. Cells were exposed to the compounds for 24 hours and cell viability was determined by MTS® assay. Data shown are representative of means ±SE of 3 independent samples. The results showed that increasing the concentrations of NACCbl and GSCbl did not affect cell viability until reaching concentrations above 0.2 mM. Above this concentration, there was a decrease in survival but even at 10 mM over 60% survival was observed in the NACCbl treated cells (FIG. 13). Above 0.2 mM concentration, GSCbl caused greater cell death than NACCbl (FIG. 13).

TABLE 14

| Variable Conc. | NACCbl | NACCbl | NACCbl | GSCbl | GSCbl | GSCbl |
|---|---|---|---|---|---|---|
| 10000 | 1.908 | 1.82 | 1.732 | 1.322 | 1.342 | 1.366 |
| 5000 | 2.081 | 2.003 | 2.004 | 1.728 | 1.67 | 1.623 |
| 2500 | 1.989 | 1.891 | 2.085 | 1.775 | 1.81 | 1.896 |
| 1250 | 2.2 | 2.055 | 2.3 | 1.973 | 1.846 | 1.71 |
| 625 | 2.358 | 2.242 | 2.347 | 2.197 | 1.912 | 1.787 |
| 312.5 | 2.409 | 2.301 | 2.437 | 2.306 | 2.204 | 2.138 |
| 156.25 | 2.484 | 2.42 | 2.492 | 2.407 | 2.37 | 2.318 |
| 78.125 | 2.521 | 2.488 | 2.475 | 2.444 | 2.406 | 2.402 |
| 39.062 | 2.503 | 2.474 | 2.453 | 2.492 | 2.484 | 2.468 |
| 19.531 | 2.485 | 2.466 | 2.502 | 2.553 | 2.476 | 2.42 |
| 9.765 | 2.505 | 2.474 | 2.514 | 2.532 | 2.476 | 2.42 |
| 4.882 | 2.532 | 2.463 | 2.457 | 2.543 | 2.528 | 2.519 |
| 2.441 | 2.592 | 2.536 | 2.499 | 2.527 | 2.434 | 2.46 |
| 1.22 | 2.546 | 2.524 | 2.538 | 2.347 | 2.433 | 2.503 |
| 0.61 | 2.572 | 2.498 | 2.473 | 2.554 | 2.376 | 2.53 |
| 0 | 2.61 | 2.688 | 2.634 | 2.487 | 2.441 | 2.52 |

Figures 14, 14A:
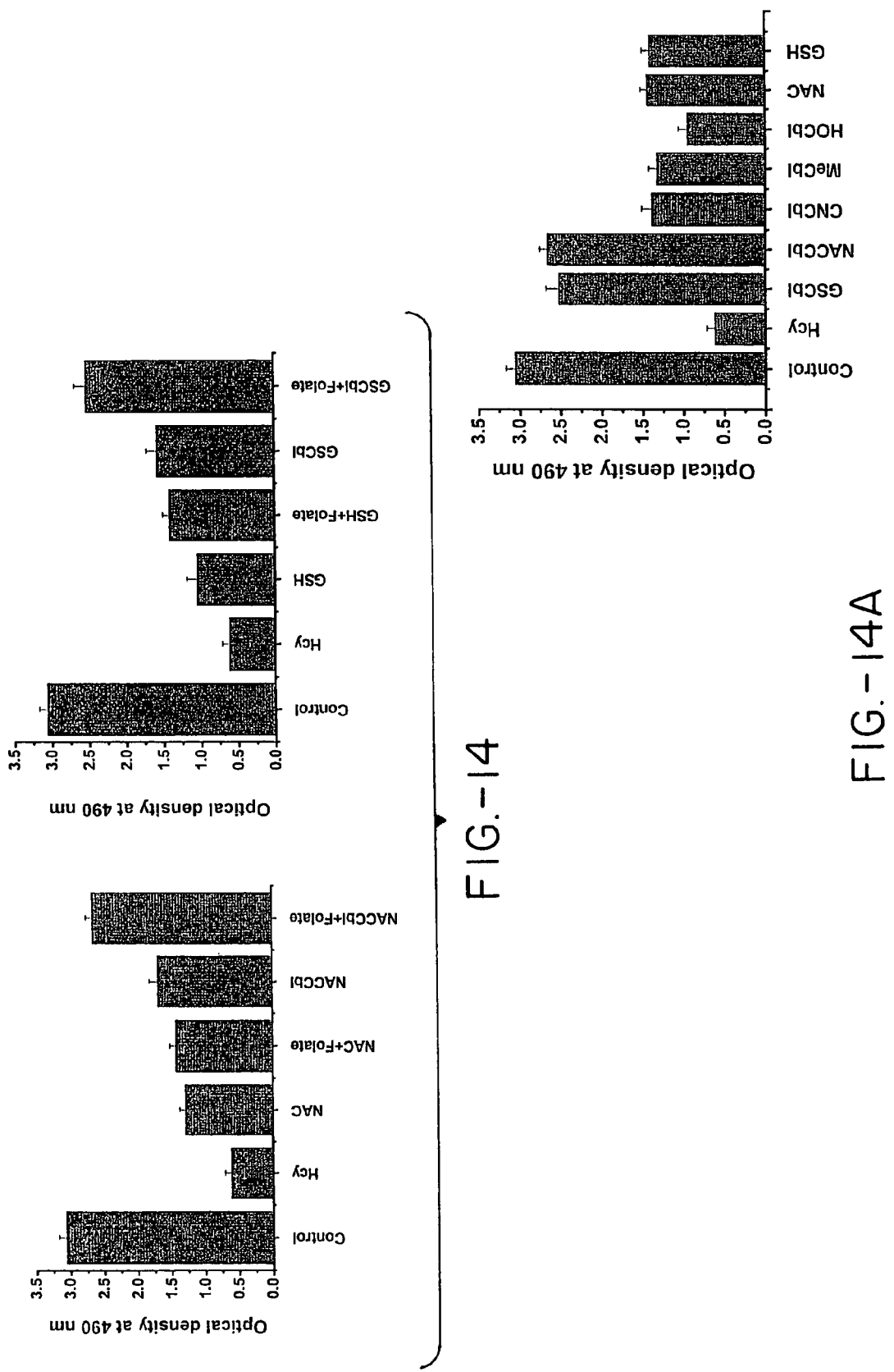
FIG. 14 illustrates the effect of the free thiols NA and GSH versus NACCbl or GSCbl in the absence or presence of folate on protecting SK-HEP-1 cells from Hcy.
FIG. 14a illustrates the effects of cobalamins in the presence of folate on protecting T SK-HEP-1 cells from Hcy.

A direct comparison of the protection against homocysteine-induced damage demonstrated that NACCbl and GSCbl are superior to the free thiols. (FIGS. 14, 14(a). FIG. 14 illustrates the effect of the free thiols NAC (45 μm) and GSH (100 μM) versus NACCbl (12.5 μM) or GSCbl (15 μM) in the absence or presence of folate (25 μm) on protecting SK-HEP-1 cells from Hcy (30 μM). FIG. 14a illustrates the effects of cobalamins in the presence of folate (25 μM) on protecting T SK-HEP-1 cells from Hcy (30 μM). GSCbl=15 μM; NACCbl=12.5 μM; CNCbl=15.0 μM; MeCbl=12.5 μM; HOCbl=15.5 μM. The protective effects of NAC (45 μM) and GSH (100 μM) in the presence of folate (25 μM) are also shown for comparison purposes.

The data is set forth below.

| Condition | [Hcy] (μM) | Mean | SDM |
|---|---|---|---|
| Control | 0 | 3.06117 | 0.10953 |
| Hcy | 30 | 0.616 | 0.09193 |
| NAC | 30 | 1.29633 | 0.07974 |
| NACCbl | 30 | 1.69583 | 0.11965 |
| NAC + Folate | 30 | 1.43783 | 0.08293 |
| NACCbl + Folate | 30 | 2.66117 | 0.09405 |

[NAC] = 45 μM
[Folate] = 25 μM
[NACCbl] = 12.5 μM

| Condition | [Hcy] (μM) | Mean | SDM |
|---|---|---|---|
| Control | 0 | 3.06117 | 0.10953 |
| Hcy | 30 | 0.616 | 0.09193 |
| NAC | 30 | 1.29633 | 0.07974 |
| NACCbl | 30 | 1.69583 | 0.11965 |
| NAC + Folate | 30 | 1.43783 | 0.08293 |
| NACCbl + Folate | 30 | 2.66117 | 0.09405 |

[NAC] = 45 μM
[Folate] = 25 μM
[NACCbl] = 12.5 μM

| Condition | [Hcy] (μM) | Mean | SDM |
|---|---|---|---|
| Control | 0 | 3.06117 | 0.10953 |
| Hcy | 30 | 0.616 | 0.09193 |
| GSCbl | 30 | 2.52433 | 0.15311 |
| NACCbl | 30 | 2.66117 | 0.09405 |
| CNCbl | 30 | 1.38333 | 0.12226 |
| MeCbl | 30 | 1.32217 | 0.10209 |
| HOCbl | 30 | 0.94983 | 0.10809 |
| NAC | 30 | 1.43783 | 0.08293 |
| GSH | 30 | 1.40933 | 0.09033 |

[GSH] = 100 μM
[NAC] = 45 μM
[Folate] = 25 μM
[GSCbl] = 15 μM;
[NACCbl] = 12.5 μM;
[CNCbl] = 15 μM;
[MeCbl] = 12.5 μM;
[HOCbl] = 17.5 μM.

Figure 15:
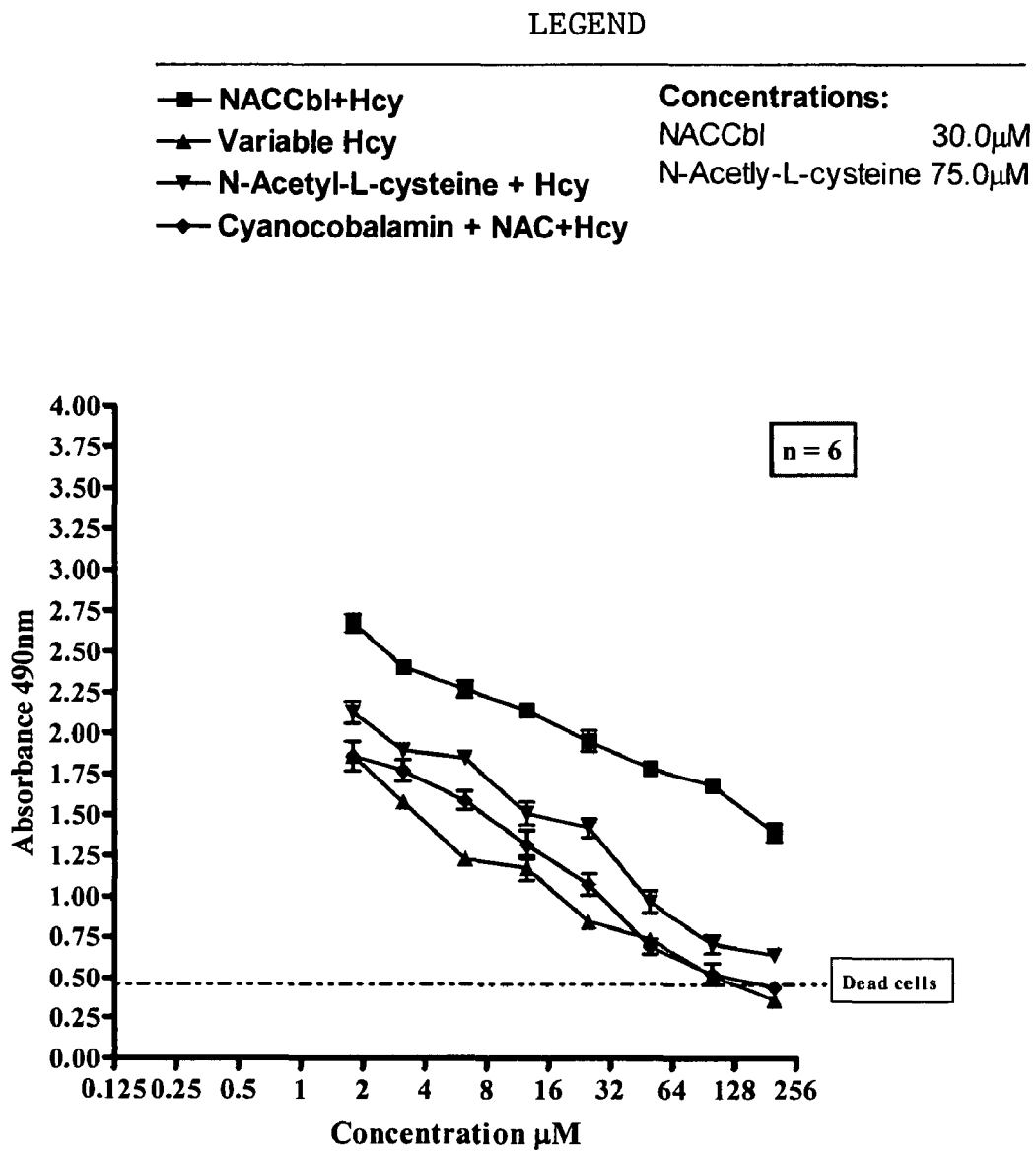
FIG. 15 illustrates the effect of variable Hcy, protection with NACCbl versus Hcy and N-acetyl-cysteine versus Hcy.
Figure 16:
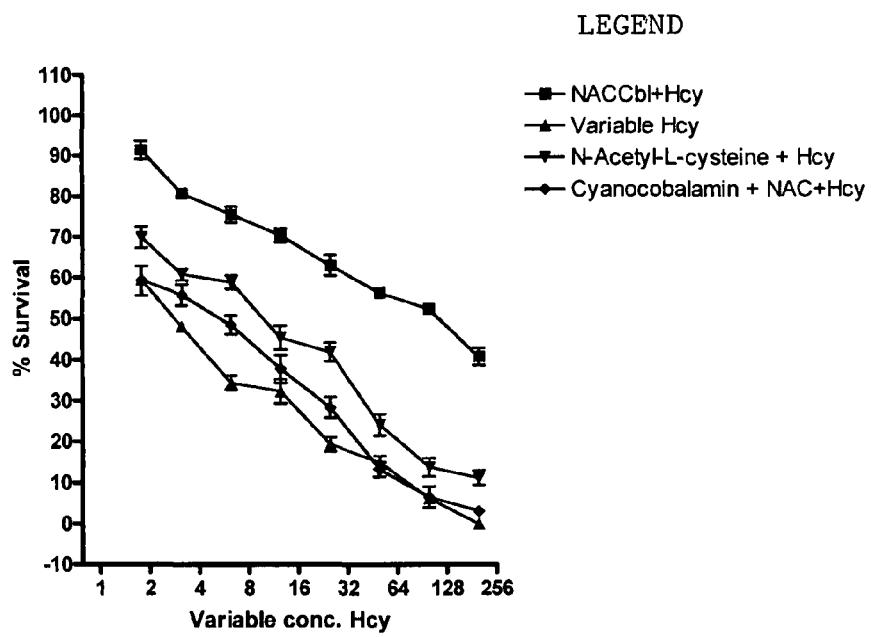
FIG. 16 illustrates the normalized raw statistical data normalized to Log 2.
Figure 17:
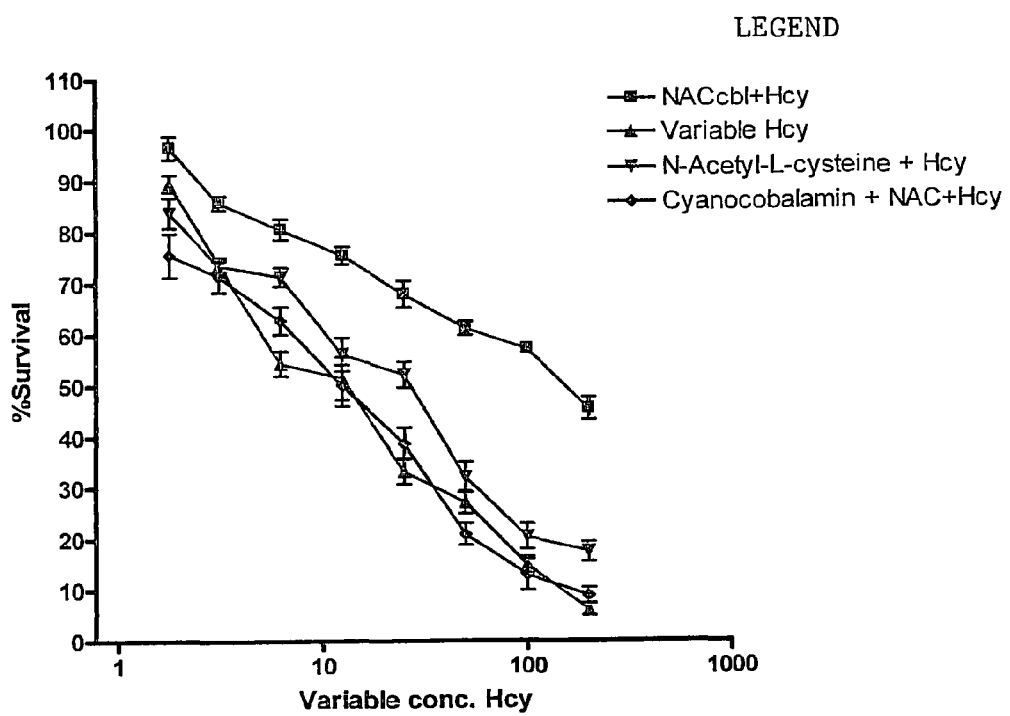
FIG. 17 illustrates the normalized raw statistical data normalized to Log 10.
Figure 19:
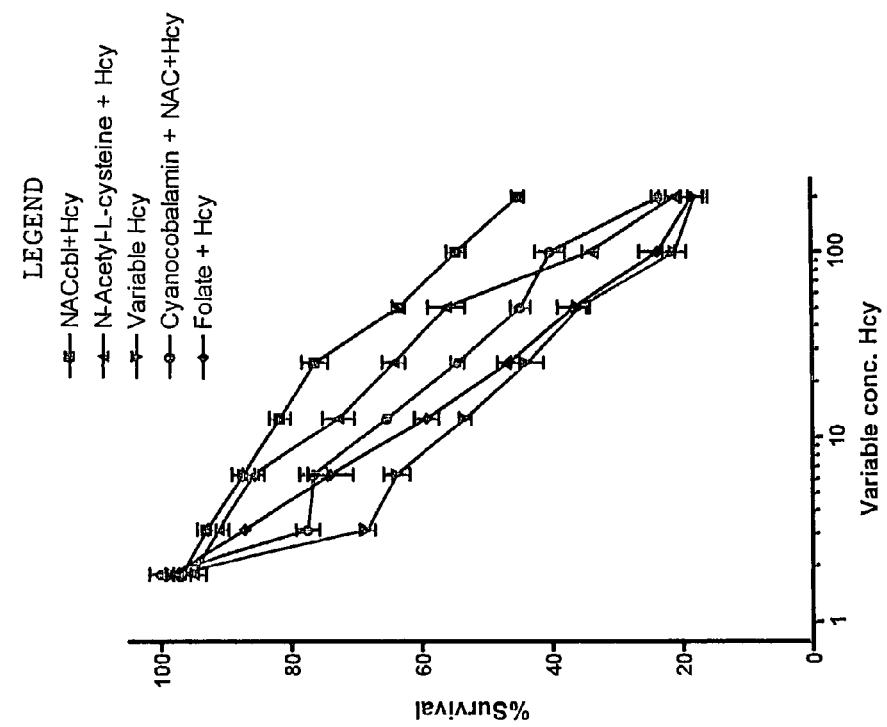
FIG. 19 illustrates percentage survival rate of Jurkat cells at a variable concentration of Hcy with the administration of various compositions.

A comparison of the protective effects of NACCbl, NAC and cyanocobalamin+NAC against variable Hcy concentration is shown in FIG. 15. The results demonstrate that NACCbl (30 μM) is superior to either NAC (75 μM) alone or in combination with CNCbl (cyanocobalamin+NAC) in preventing cell death. Table 15 and Table 15 (a) below show the results for cell death as characterized by absorbance at 490 nm for NACCbl, variable Hcy, NAC and cyanocobalamin+NAC. The data was normalized (log 2 and log 10) as shown in FIGS. 16 and 17 and Tables 16 and 17, respectively, below. Normalization reflects that protection with NACCbl is superior to that of NAC or cyanocobalamin+NAC.

TABLE 15

Absorbance at 490 nm (n = 6)

| Variable | Variable Hcy | | | | | |
|---|---|---|---|---|---|---|
| Conc. of Hcy | Y1 | Y2 | Y3 | Y4 | Y5 | Y6 |
| 200.000 | 0.330 | 0.312 | 0.390 | 0.302 | 0.421 | 0.406 |
| 100.000 | 0.654 | 0.449 | 0.466 | 0.501 | 0.522 | 0.510 |
| 50.000 | 0.678 | 0.881 | 0.602 | 0.770 | 0.724 | 0.779 |
| 25.000 | 0.692 | 0.956 | 0.876 | 0.882 | 0.937 | 0.740 |
| 12.500 | 1.104 | 1.001 | 1.042 | 1.114 | 1.324 | 1.479 |
| 6.250 | 1.304 | 1.406 | 1.227 | 1.176 | 1.150 | 1.119 |
| 3.125 | 1.543 | 1.487 | 1.656 | 1.630 | 1.593 | 1.558 |
| 1.780 | 1.746 | 1.932 | 1.950 | 1.830 | 1.837 | 1.884 |
| 0.000 | 2.109 | 2.110 | 1.999 | 2.056 | 2.100 | 1.936 |

| Variable | NACCbl + Hcy | | | | | |
|---|---|---|---|---|---|---|
| Conc. of Hcy | Y1 | Y2 | Y3 | Y4 | Y5 | Y6 |
| 200.000 | 1.378 | 1.167 | 1.330 | 1.456 | 1.491 | 1.537 |
| 100.000 | 1.678 | 1.592 | 1.694 | 1.773 | 1.732 | 1.639 |
| 50.000 | 1.678 | 1.832 | 1.881 | 1.730 | 1.740 | 1.855 |
| 25.000 | 2.100 | 2.190 | 1.879 | 1.937 | 1.779 | 1.837 |
| 12.500 | 2.210 | 2.110 | 2.045 | 2.065 | 2.101 | 2.324 |
| 6.250 | 2.410 | 2.400 | 2.322 | 2.201 | 2.115 | 2.187 |
| 3.125 | 2.453 | 2.338 | 2.360 | 2.317 | 2.418 | 2.535 |
| 1.780 | 2.647 | 2.551 | 2.789 | 2.890 | 2.549 | 2.611 |
| 0.000 | 2.885 | 2.698 | 2.821 | 2.771 | 2.691 | 2.700 |

| Variable | N-Acetyl-L-cysteine + Hcy | | | | | |
|---|---|---|---|---|---|---|
| Conc. of Hcy | Y1 | Y2 | Y3 | Y4 | Y5 | Y6 |
| 200.000 | 0.567 | 0.668 | 0.623 | 0.490 | 0.721 | 0.788 |
| 100.000 | 0.789 | 0.842 | 0.743 | 0.589 | 0.490 | 0.799 |
| 50.000 | 0.890 | 0.821 | 1.034 | 1.227 | 0.799 | 1.045 |
| 25.000 | 1.345 | 1.501 | 1.632 | 1.378 | 1.226 | 1.447 |
| 12.500 | 1.675 | 1.232 | 1.339 | 1.590 | 1.602 | 1.622 |
| 6.250 | 1.678 | 1.789 | 1.897 | 1.899 | 1.933 | 1.905 |
| 3.725 | 1.890 | 2.003 | 1.784 | 1.946 | 1.958 | 1.801 |
| 1.780 | 2.225 | 1.903 | 1.947 | 2.310 | 2.187 | 2.206 |
| 0.000 | 2.592 | 2.476 | 2.437 | 2.678 | 2.336 | 2.447 |

TABLE 15-continued

Absorbance at 490 nm (n = 6)

| Variable | Cyanocobalamin + NAC + Hcy | | | | | |
|---|---|---|---|---|---|---|
| Conc. of Hcy | Y1 | Y2 | Y3 | Y4 | Y5 | Y6 |
| 200.000 | 0.345 | 0.421 | 0.456 | 0.567 | 0.378 | 0.471 |
| 100.000 | 0.789 | 0.634 | 0.456 | 0.447 | 0.336 | 0.490 |
| 50.000 | 0.890 | 0.576 | 0.678 | 0.732 | 0.602 | 0.693 |
| 25.000 | 1.345 | 0.898 | 0.936 | 1.121 | 1.044 | 1.117 |
| 12.500 | 1.675 | 1.056 | 1.210 | 1.226 | 1.402 | 1.339 |
| 6.250 | 1.678 | 1.538 | 1.336 | 1.669 | 1.722 | 1.590 |
| 3.725 | 1.890 | 1.578 | 1.773 | 1.609 | 1.793 | 1.993 |
| 1.780 | 2.225 | 1.567 | 1.875 | 1.690 | 1.884 | 1.921 |
| 0.000 | 2.592 | 2.389 | 2.449 | 2.201 | 2.108 | 2.557 |

TABLE 15(a)

Statistical Analysis (n = 6)
Absorbance at 490 nm

| Variable | NACCbl + Hcy | | Variable Hcy | | N-Acetyl-L-cysteine + Hcy | | Cyanocobalamin + NAC + Hcy | |
|---|---|---|---|---|---|---|---|---|
| Conc. Hcy | Mean | SEM | Mean | SEM | Mean | SEM | Mean | SEM |
| 200.000 | 1.393 | 0.055 | 0.360 | 0.021 | 0.643 | 0.044 | 0.440 | 0.032 |
| 100.000 | 1.685 | 0.026 | 0.517 | 0.030 | 0.709 | 0.057 | 0.525 | 0.066 |
| 50.000 | 1.786 | 0.033 | 0.739 | 0.039 | 0.969 | 0.067 | 0.695 | 0.046 |
| 25.000 | 1.954 | 0.065 | 0.847 | 0.044 | 1.421 | 0.057 | 1.077 | 0.065 |
| 12.500 | 2.142 | 0.043 | 1.177 | 0.076 | 1.510 | 0.073 | 1.318 | 0.086 |
| 6.250 | 2.273 | 0.050 | 1.230 | 0.044 | 1.850 | 0.040 | 1.589 | 0.057 |
| 3.125 | 2.404 | 0.033 | 1.578 | 0.025 | 1.897 | 0.036 | 1.773 | 0.065 |
| 1.780 | 2.673 | 0.056 | 1.863 | 0.031 | 2.130 | 0.067 | 1.860 | 0.092 |
| 0.000 | 2.761 | 0.032 | 2.052 | 0.029 | 2.494 | 0.050 | 2.383 | 0.079 |

TABLE 16

Normalized Data Log 2 (n = 6)

| Variable | NACCbl + Hcy | | Variable Hcy | | N-Acetyl-L-cysteine + Hcy | | Cyanocobalamin + NAC + Hcy | |
|---|---|---|---|---|---|---|---|---|
| Conc. Hcy | Mean | SEM | Mean | SEM | Mean | SEM | Mean | SEM |
| 200.000 | 40.781 | 2.159 | −0.033 | 0.832 | 11.135 | 1.727 | 3.108 | 1.261 |
| 100.000 | 52.298 | 1.042 | 6.164 | 1.170 | 13.738 | 2.233 | 6.493 | 2.595 |
| 50.000 | 56.302 | 1.307 | 14.935 | 1.538 | 24.035 | 2.637 | 13.203 | 1.803 |
| 25.000 | 62.926 | 2.573 | 19.208 | 1.730 | 41.900 | 2.249 | 28.283 | 2.585 |
| 12.500 | 70.387 | 1.704 | 32.253 | 2.986 | 45.397 | 2.896 | 37.811 | 3.412 |
| 6.250 | 75.524 | 1.973 | 34.347 | 1.739 | 58.837 | 1.578 | 48.512 | 2.265 |
| 3.125 | 80.699 | 1.323 | 48.077 | 0.992 | 60.687 | 1.432 | 55.775 | 2.575 |
| 1.780 | 91.341 | 2.227 | 59.351 | 1.212 | 69.880 | 2.655 | 59.239 | 3.625 |
| 0.000 | 94.824 | 1.284 | 66.798 | 1.145 | 84.288 | 1.965 | 79.876 | 3.120 |

TABLE 17

| | | | | | N-Acetyl-L- | | Cyanocobalamin + | |
| Variable | NACCbl + Hcy | | Variable Hcy | | cysteine + Hcy | | NAC + Hcy | |
| Conc. Hcy | Mean | SEM | Mean | SEM | Mean | SEM | Mean | SEM |
|---|---|---|---|---|---|---|---|---|
| 200.000 | 45.526 | 2.176 | 6.115 | 1.169 | 17.503 | 1.948 | 8.893 | 1.497 |
| 100.000 | 57.135 | 1.050 | 14.820 | 1.644 | 20.439 | 2.518 | 12.910 | 3.079 |
| 50.000 | 61.171 | 1.317 | 27.142 | 2.160 | 32.051 | 2.974 | 20.874 | 2.140 |
| 25.000 | 67.848 | 2.594 | 33.145 | 2.430 | 52.198 | 2.537 | 38.770 | 3.067 |
| 12.500 | 75.368 | 1.717 | 51.471 | 4.194 | 56.141 | 3.266 | 50.078 | 4.049 |
| 6.250 | 80.546 | 1.989 | 54.413 | 2.443 | 71.298 | 1.779 | 62.777 | 2.688 |
| 3.125 | 85.763 | 1.333 | 73.700 | 1.394 | 73.385 | 1.615 | 71.397 | 3.056 |
| 1.780 | 96.489 | 2.245 | 89.537 | 1.702 | 83.752 | 2.994 | 75.508 | 4.302 |
| 0.000 | 100.000 | 1.294 | 100.000 | 1.609 | 100.000 | 2.216 | 100.000 | 3.703 |

Figure 18:
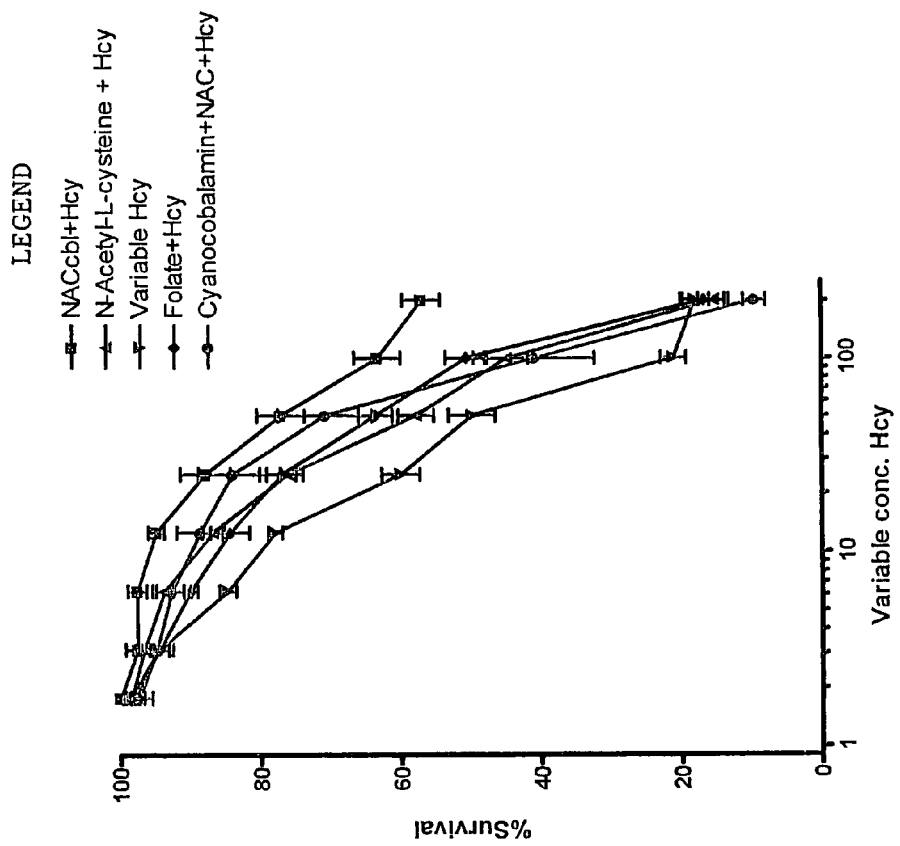
FIG. 18 illustrates percentage survival rate of U937 cells at a variable concentration of Hcy with the administration of various compositions.

Additional cell studies were conducted using Jurkat (T-cells) and U937 (monocyte) cell lines. These experiments confirmed that other cell types are killed by homocysteine, although these cell lines are not as sensitive as the SK-HEP-1 cell line discussed in the experiments above and are thus more resistant to homocysteine. Cells were exposed to NACCbl 30 μM, NAC 75 μM, CNCbl 15 μM, and folate 30 μM. Data set forth in FIGS. 18 (U937) and 19 (Jurkat cells) showed that NACCbl is more effective at protecting these cells from death than NAC, CN Cbl or folate, especially at higher homocysteine concentrations, and that the protective effect is not just limited to SK-HEP-1 cells. In these Figures, the monocytes are N=6 and concentrations are as follows: NACCbl 30 μM, NAC 75 μM, CNCbl 15 μM, Folate 30 μM

CONCLUSIONS

NACCbl has been shown to be stable and biologically active and to protect cells from oxidative stress damage. This novel, synthetic thiolatocobalamin was more effective than any of the other cobalamins in this activity for both homocysteine and $H_2O_2$-induced oxidative stress.

It will be understood by those who practice the invention and those skilled in the art that various modifications and improvements may be made to the invention without departing from the spirit of the disclosed concept. The scope of protection afforded is to be determined by the claims and by the breadth of interpretation allowed by law.

The invention claimed is:

1. A method of reducing serum homocysteine levels or treating one or more of cardiovascular disease, cerebrovascular disease, peripheral vascular disease, glaucoma, Alzheimer's disease, and dementia, in an animal selected from the group of livestock, a domestic animal or a human comprising administering an effective amount of N-acetyl-L-cysteinylcobalamin.

2. The method according to claim 1 further comprising administering said N-acetyl-L-cysteinylcobalamin in combination with one or more of a folate compound and vitamin $B_6$.

3. The method according to claim 2 wherein said folate compound is selected from the group consisting of folate, (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives.

4. The method according to claim 2 in which N-acetyl-L-cysteinylcobalamin is administered with vitamin $B_6$.

5. A method of reducing high homocysteine levels or of reducing free radical formation levels in a subject animal comprising livestock, a domestic animal or a human comprising administering an effective amount of N-acetyl-L-cysteinylcobalamin to the subject animal.

6. A method according to claim 5 further comprising administering said N-acetyl-L-cysteinylcobalamin in combination with one or more of a folate compound and vitamin $B_6$.

7. The method according to claim 6 wherein said folate compound is selected from the group consisting of folate, (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives.

8. A pharmaceutical composition comprising N-acetyl-L-cysteinylcobalamin and one or more of a folate compound and vitamin $B_6$.

9. A pharmaceutical composition according to claim 8 wherein said N-acetyl-L-cysteinylcobalarnin comprises a crystalline salt of N-acetyl-L-cysteinylcobalamin.

10. The pharmaceutical composition according to claim 9 wherein said crystalline salt is a sodium salt of said N-acetyl-L-cysteinylcobalamin.

11. The pharmaceutical composition according to claim 8 wherein the folate compound is folate or a natural isomer of reduced folate.

12. The pharmaceutical composition according to claim 11 wherein the natural isomer of reduced folate is one or more of (6S)-tetrahydrofolic acid, 5-methyl-(68)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives.

13. The pharmaceutical composition according to claim 8 further comprising vitamin $B_6$.

14. A dietary supplement comprising N-acetyl-L-cysteinylcobalamin and one of more of a folate compound and vitamin $B_6$.

15. The dietary supplement according to claim 14 further comprising a crystalline salt of N-acetyl-L-cysteinylcobalamin.

16. The dietary supplement according to claim 15 wherein said crystalline salt is a potassium or sodium salt of said N-acetyl-L-cysteinylcobalamin.

17. The pharmaceutical composition according to claim 14 wherein the folate compound is selected from the group consisting of folate, (6S)-tetrahydrofolic acid, 5-methyl-(6S)-tetrahyclrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and their polyglutamyl derivatives.

* * * * *